United States Patent
Yeh et al.

(10) Patent No.: US 11,918,000 B2
(45) Date of Patent: Mar. 5, 2024

(54) METHODS FOR INDUCING RESISTANCE TO VIRUS IN A PLANT, PRIMING A PLANT TO RESIST VIRUSES, DECREASING VIRUS ACCUMULATION, OR INCREASING PR1 EXPRESSION IN A PLANT

(71) Applicant: Academia Sinica, Taipei (TW)

(72) Inventors: Hsin-Hung Yeh, Keelung (TW); Yi-Shu Chiu, Yilan County (TW)

(73) Assignee: ACADEMIA SINICA, Taipei (TW)

( * ) Notice: Subject to any disclaimer, the term of this patent is extended or adjusted under 35 U.S.C. 154(b) by 1024 days.

(21) Appl. No.: 16/432,230

(22) Filed: Jun. 5, 2019

(65) Prior Publication Data

US 2020/0383335 A1    Dec. 10, 2020

(51) Int. Cl.
| | | |
|---|---|---|
| *A01N 63/30* | (2020.01) | |
| *A01N 63/32* | (2020.01) | |
| *C08B 37/00* | (2006.01) | |
| *C12N 1/14* | (2006.01) | |
| *C12N 1/16* | (2006.01) | |
| *C12R 1/645* | (2006.01) | |

(52) U.S. Cl.
CPC .............. *A01N 63/30* (2020.01); *A01N 63/32* (2020.01); *C08B 37/0087* (2013.01); *C12N 1/145* (2021.05); *C12N 1/165* (2021.05); *C12R 2001/645* (2021.05)

(58) Field of Classification Search
None
See application file for complete search history.

(56) References Cited

U.S. PATENT DOCUMENTS

2013/0045510 A1* 2/2013 Yu ................... C12P 19/02
435/320.1

OTHER PUBLICATIONS

Office Action and Search Report in Taiwan Counterpart Application No. 108119461, dated Aug. 6, 2020, in 5 pages; English translation provided.
Gutierrez et al., "Structural Characterization of Extracellular Polysaccharides Produced by Fungi from the Genus *Pleurotus*," Carbohydrate Research, 1996, 281(1), pp. 143-154.
Pieterse, Corné MJ, et al. "Hormonal modulation of plant immunity." Annual Review of Cell and Developmental Biology 28 (2012): 489-521.
Pieterse, Corné MJ, et al. "Induced systemic resistance by beneficial microbes." Annual Review of Phytopathology 52 (2014): 347-375.
Mauch-Mani, Brigitte, et al. "Defense priming: an adaptive part of induced resistance." Annual Review of Plant Biology 68 (2017): 485-512.
Chiu YS, et al. "A Polysaccharide Derived from a *Trichosporon* sp. Culture Strongly Primes Plant Resistance to Viruses." Mol Plant Microbe Interact. Dec. 2018;31(12):1257-1270.

* cited by examiner

*Primary Examiner* — Christian L Fronda
(74) *Attorney, Agent, or Firm* — DUANE MORRIS LLP

(57) ABSTRACT

The present disclosure relates to fungi, a culture filtrate thereof and a polysaccharide and their applications in inducing or priming plant resistance to viruses. Aspects of the present disclosure provides a cultured filtrate, derived from a fungus belonging to the genus *Trichosporon*, induces strong resistance to various viruses on different plants.

9 Claims, 15 Drawing Sheets
(12 of 15 Drawing Sheet(s) Filed in Color)

Specification includes a Sequence Listing.

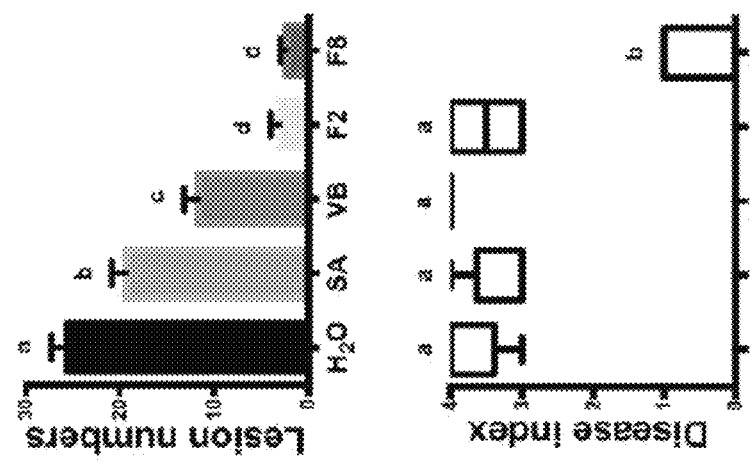
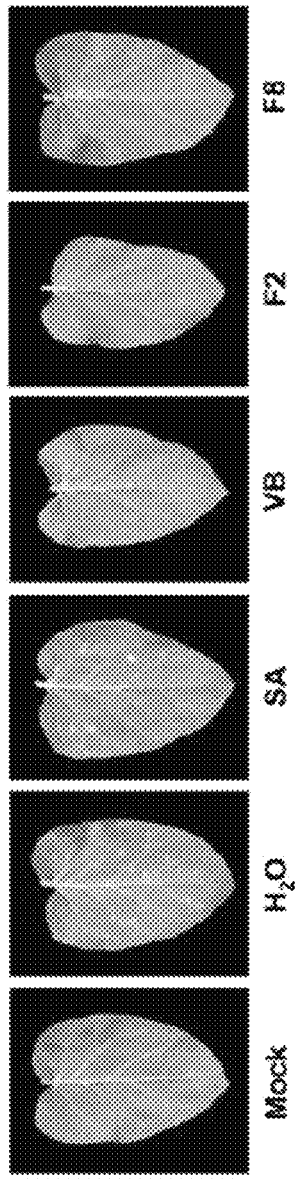
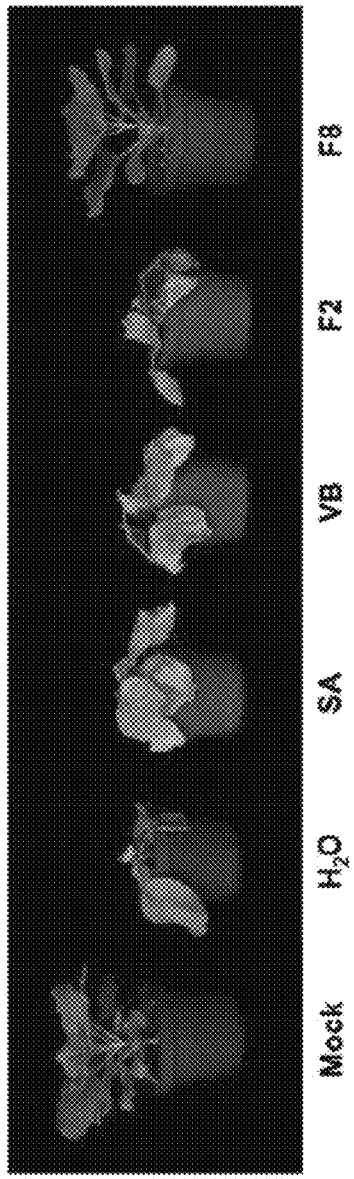
FIG. 1

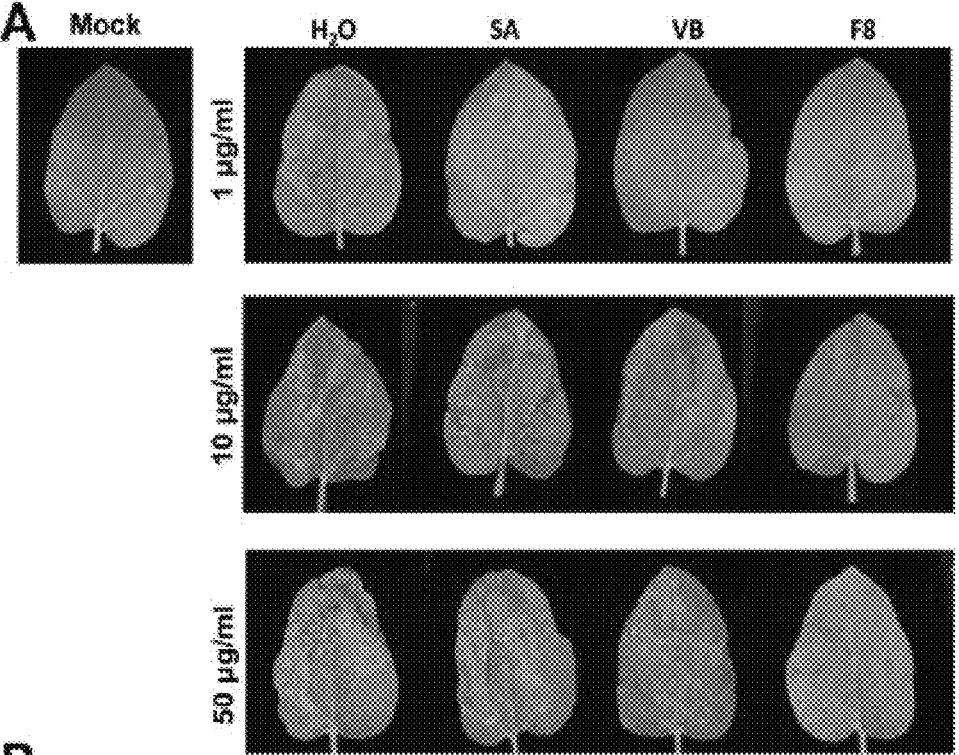
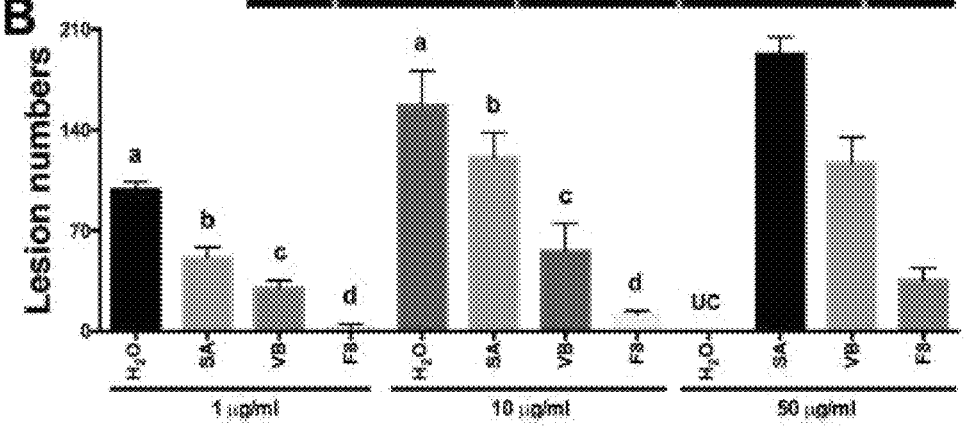
FIG. 2

FIG. 3A
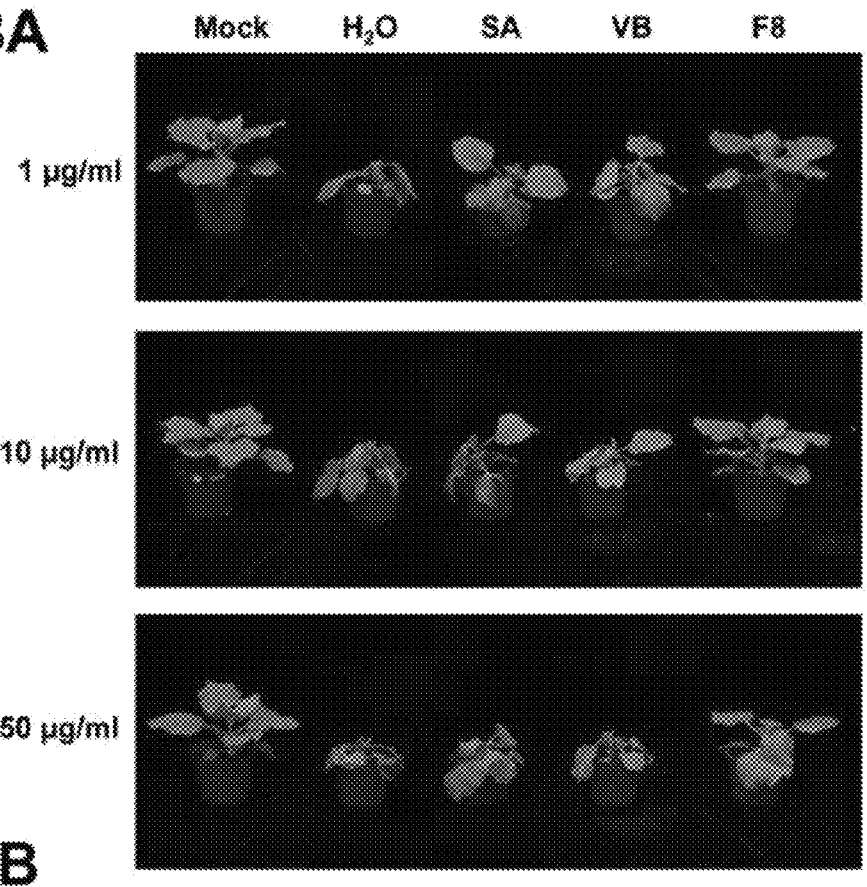
FIG. 3B
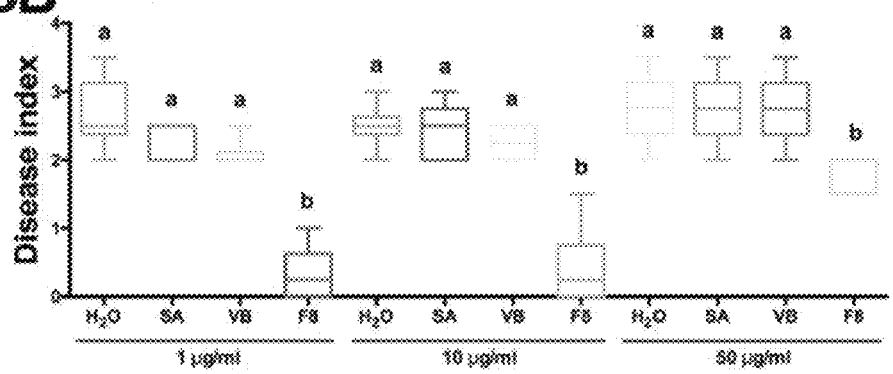
FIG. 3

FIG. 4A
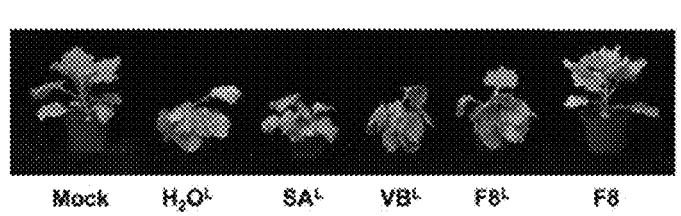
FIG. 4B
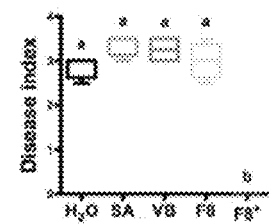
FIG. 4C
FIG. 4D
FIG. 4E
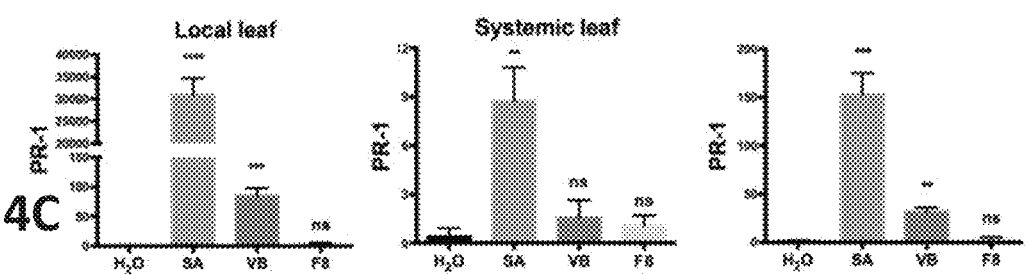
FIG. 4F
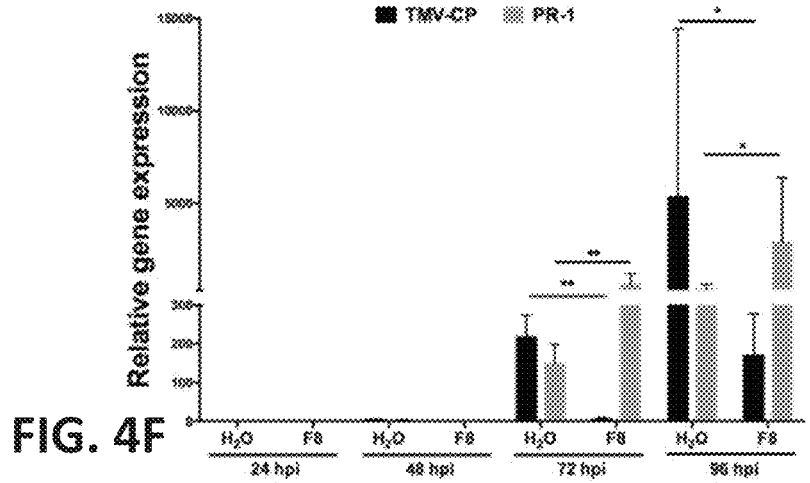
FIG. 4

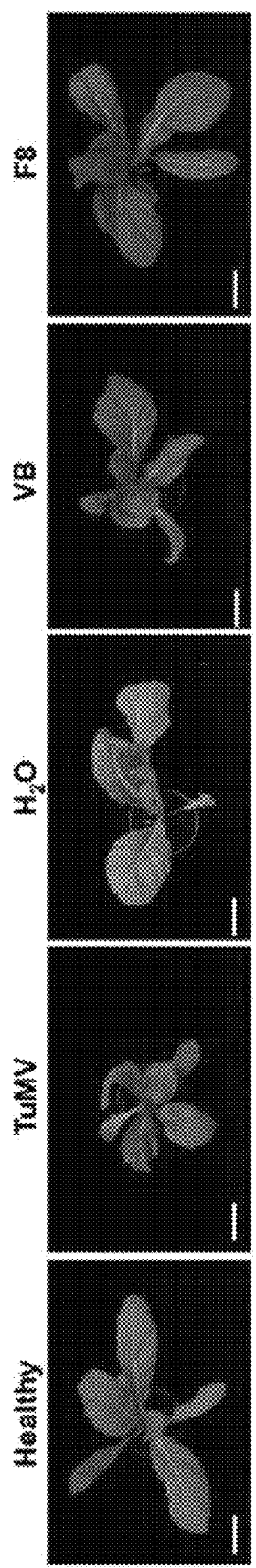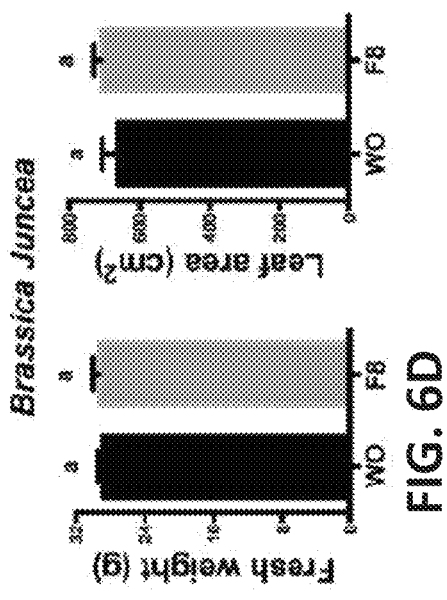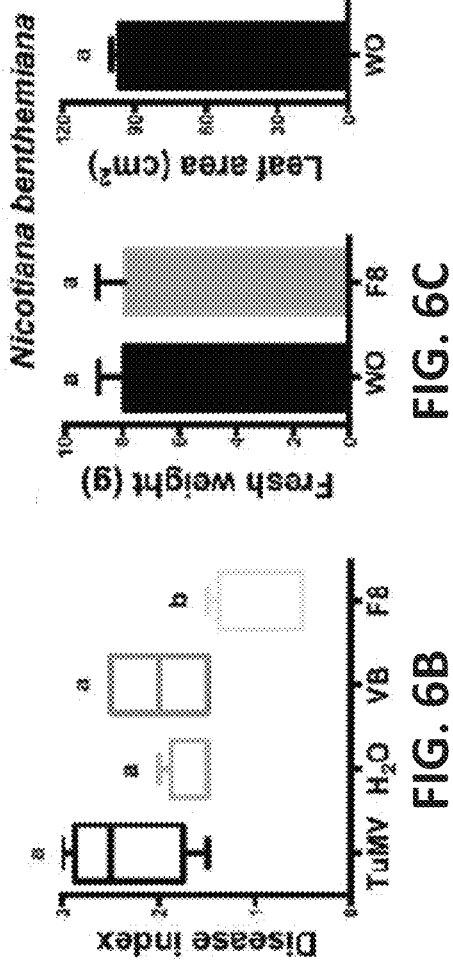
FIG. 6

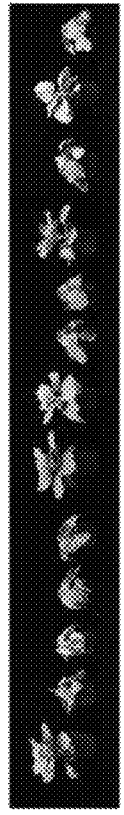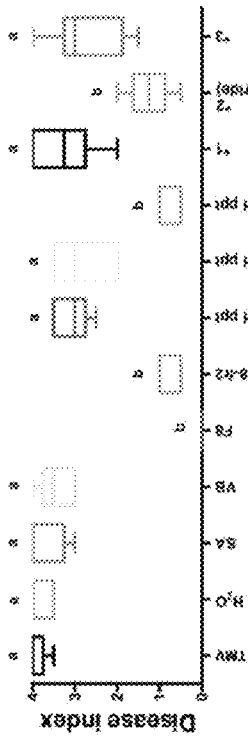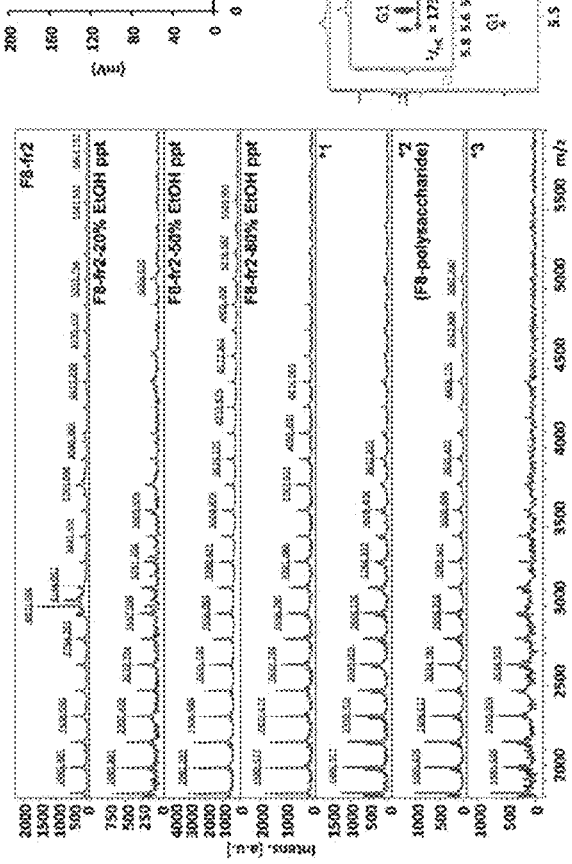
FIG. 8

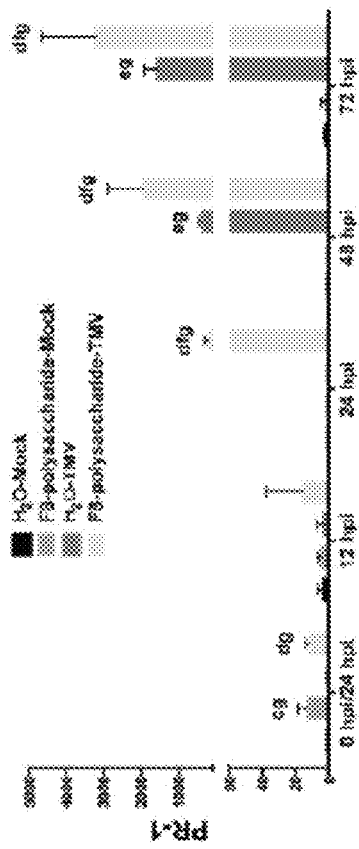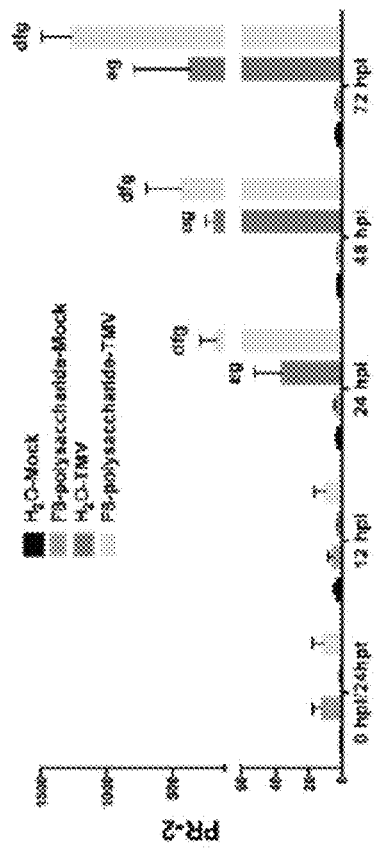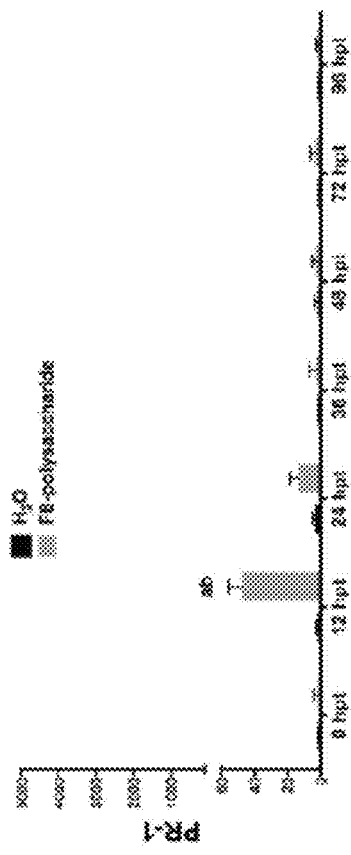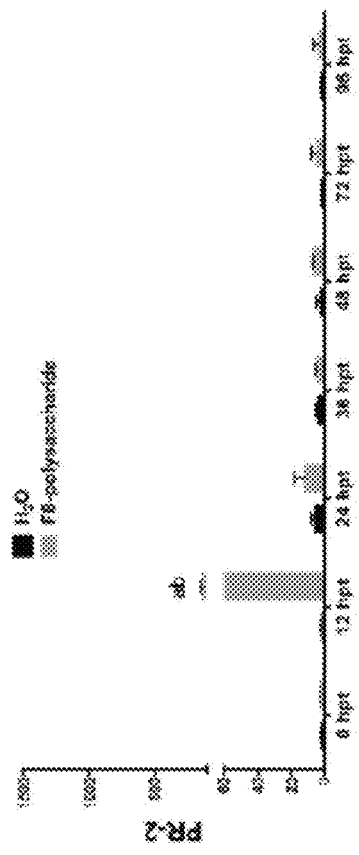
FIG. 9A  FIG. 9B  FIG. 9C  FIG. 9D
FIG. 9

FIG. 11A
H₂O  SA  VB  F8  F8-pellet  2*F8-pellet
FIG. 11B
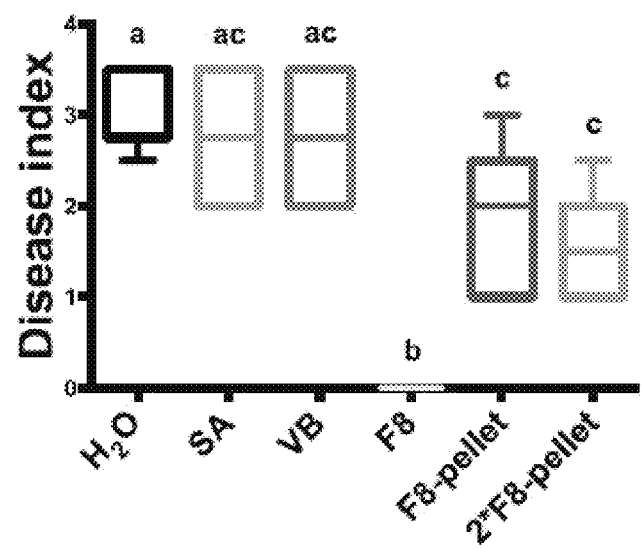
Fig. 11

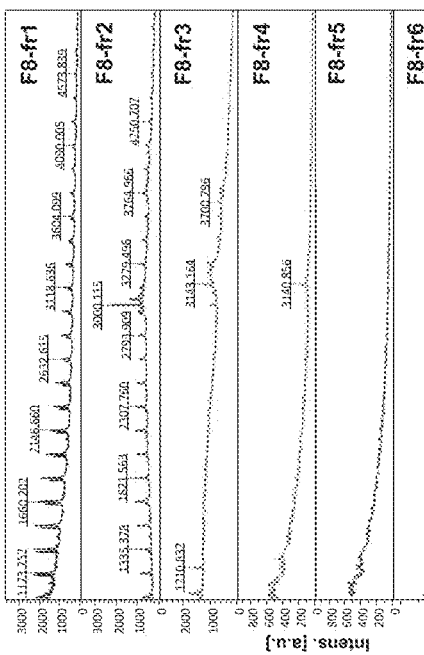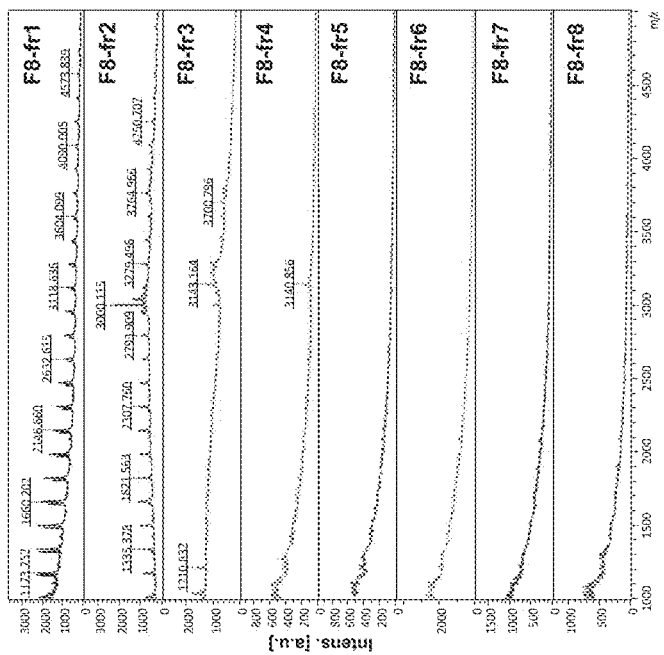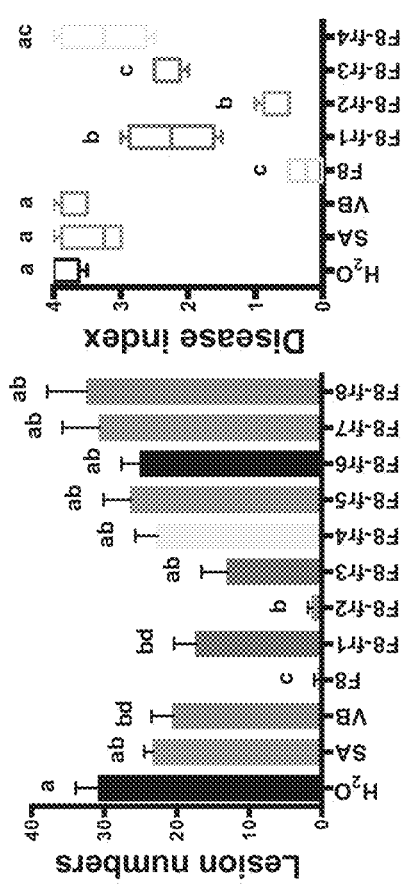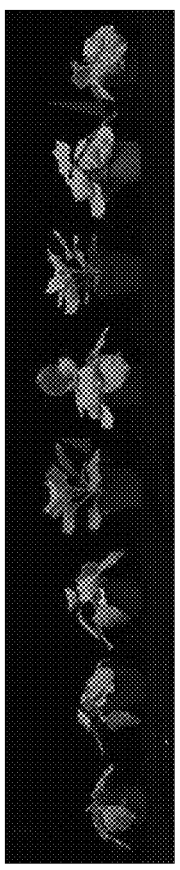
FIG. 12

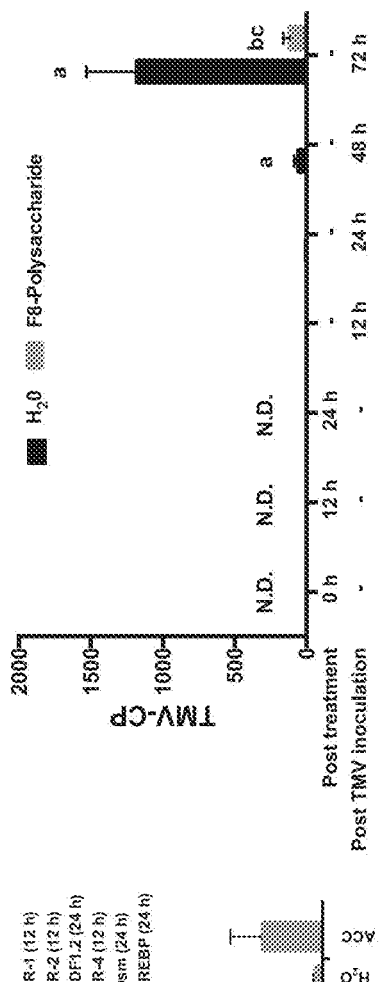
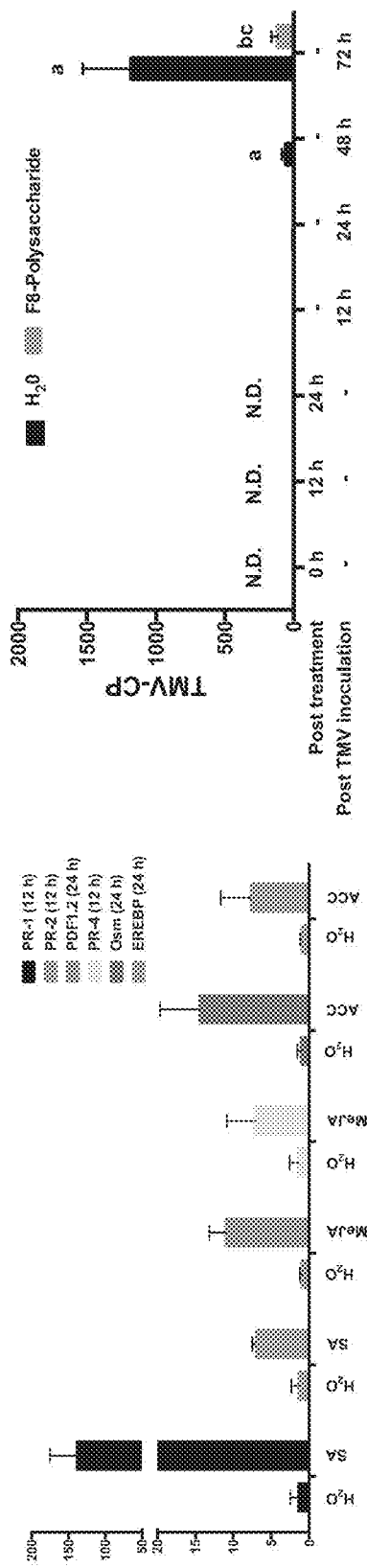
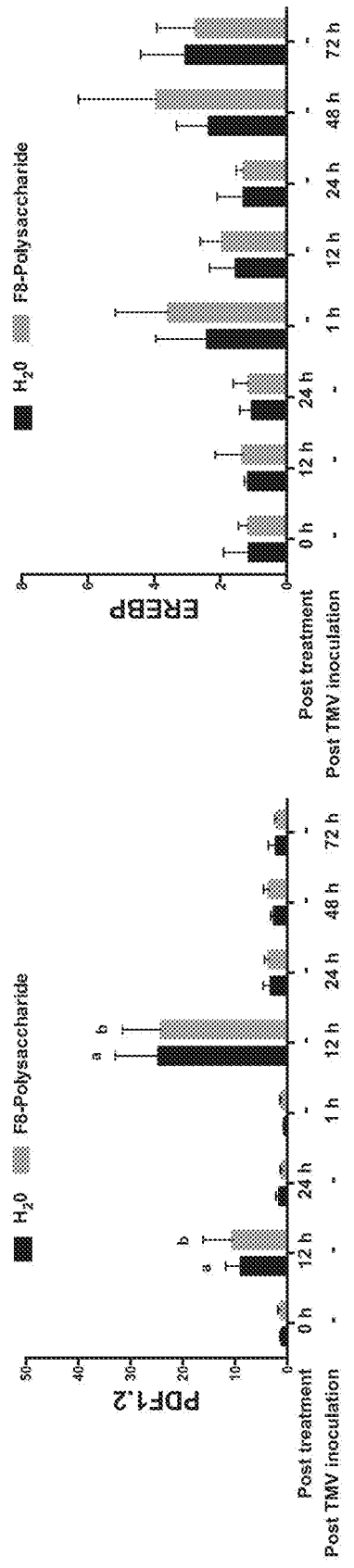
FIG. 14

FIG. 15A
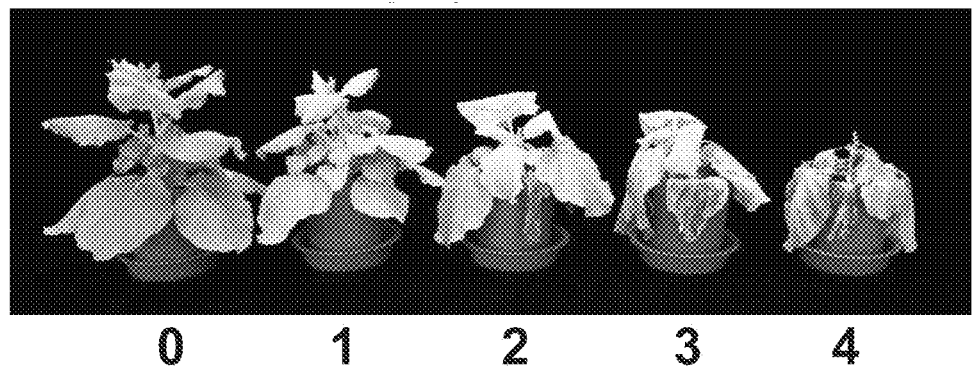
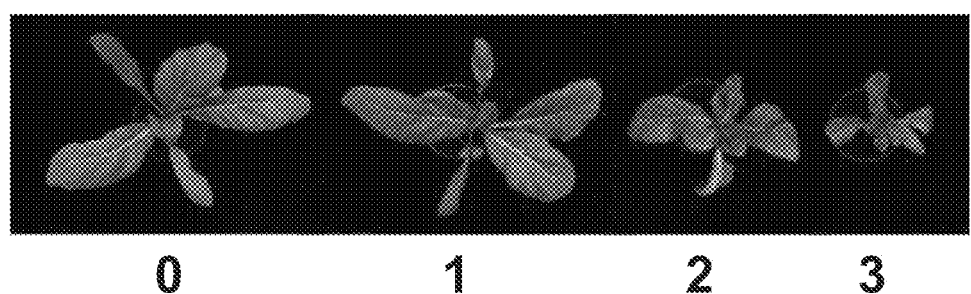
FIG. 15B
FIG. 15

SEQUENCE LISTING

```
<160> NUMBER OF SEQ ID NOS: 24

<210> SEQ ID NO 1
<211> LENGTH: 20
<212> TYPE: DNA
<213> ORGANISM: Artificial sequence
<220> FEATURE:
<223> OTHER INFORMATION: synthetic oligonucleotide

<400> SEQUENCE: 1
cgtgttcttg tcatcagcgt                                              20

<210> SEQ ID NO 2
<211> LENGTH: 20
<212> TYPE: DNA
<213> ORGANISM: artificial sequence
<220> FEATURE:
<223> OTHER INFORMATION: synthetic oligonucleotide

<400> SEQUENCE: 2
gcatctaacg tttcggcagt                                              20

<210> SEQ ID NO 3
<211> LENGTH: 20
<212> TYPE: DNA
<213> ORGANISM: artificial sequence
<220> FEATURE:
<223> OTHER INFORMATION: synthetic oligonucleotide

<400> SEQUENCE: 3
tacaagacgc gtgctgaagt                                              20

<210> SEQ ID NO 4
<211> LENGTH: 19
<212> TYPE: DNA
<213> ORGANISM: artificial sequence
<220> FEATURE:
<223> OTHER INFORMATION: synthetic oligonucleotide
```

```
<400> SEQUENCE: 4
caatgttgtg gcgaatttt                                              19

<210> SEQ ID NO 5
<211> LENGTH: 25
<212> TYPE: DNA
<213> ORGANISM: artificial sequence
<220> FEATURE:
<223> OTHER INFORMATION: synthetic oligonucleotide

<400> SEQUENCE: 5
acgaactggt gatgcattta cttat                                       25

<210> SEQ ID NO 6
<211> LENGTH: 25
<212> TYPE: DNA
<213> ORGANISM: artificial sequence
<220> FEATURE:
<223> OTHER INFORMATION: synthetic oligonucleotide

<400> SEQUENCE: 6
ttccgaagaa acctaggaga tggtt                                       25

<210> SEQ ID NO 7
<211> LENGTH: 29
<212> TYPE: DNA
<213> ORGANISM: artificial sequence
<220> FEATURE:
<223> OTHER INFORMATION: synthetic oligonucleotide

<400> SEQUENCE: 7
ttagaggaag taaaagtcgt aacaaggtt                                   29

<210> SEQ ID NO 8
<211> LENGTH: 25
<212> TYPE: DNA
<213> ORGANISM: artificial sequence
<220> FEATURE:
<223> OTHER INFORMATION: synthetic oligonucleotide

<400> SEQUENCE: 8
tcctccgctt attgatatgc ttaag                                       25

<210> SEQ ID NO 9
<211> LENGTH: 24
<212> TYPE: DNA
<213> ORGANISM: artificial sequence
<220> FEATURE:
<223> OTHER INFORMATION: synthetic oligonucleotide

<400> SEQUENCE: 9
gcatatcaat aagcggagga aaag                                        24

<210> SEQ ID NO 10
<211> LENGTH: 19
<212> TYPE: DNA
<213> ORGANISM: artificial sequence
<220> FEATURE:
<223> OTHER INFORMATION: synthetic oligonucleotide

<400> SEQUENCE: 10
ggtccgtgtt tcaagacgg                                              19

<210> SEQ ID NO 11
```

```
<211> LENGTH: 17
<212> TYPE: DNA
<213> ORGANISM: artificial sequence
<220> FEATURE:
<223> OTHER INFORMATION: synthetic oligonucleotide

<400> SEQUENCE: 11
atgcccataa cagctcg                                              17

<210> SEQ ID NO 12
<211> LENGTH: 20
<212> TYPE: DNA
<213> ORGANISM: artificial sequence
<220> FEATURE:
<223> OTHER INFORMATION: synthetic oligonucleotide

<400> SEQUENCE: 12
gaggatcata gttgcaagag                                           20

<210> SEQ ID NO 13
<211> LENGTH: 19
<212> TYPE: DNA
<213> ORGANISM: artificial sequence
<220> FEATURE:
<223> OTHER INFORMATION: synthetic oligonucleotide

<400> SEQUENCE: 13
ggtgtttgct atggaatgc                                            19

<210> SEQ ID NO 14
<211> LENGTH: 19
<212> TYPE: DNA
<213> ORGANISM: artificial sequence
<220> FEATURE:
<223> OTHER INFORMATION: synthetic oligonucleotide

<400> SEQUENCE: 14
tctgtaccca ccatcttgc                                            19

<210> SEQ ID NO 15
<211> LENGTH: 21
<212> TYPE: DNA
<213> ORGANISM: artificial sequence
<220> FEATURE:
<223> OTHER INFORMATION: synthetic oligonucleotide

<400> SEQUENCE: 15
ggaaatggca aactccatgc g                                         21

<210> SEQ ID NO 16
<211> LENGTH: 20
<212> TYPE: DNA
<213> ORGANISM: artificial sequence
<220> FEATURE:
<223> OTHER INFORMATION: synthetic oligonucleotide

<400> SEQUENCE: 16
atccttcggt cagacaaacg                                           20

<210> SEQ ID NO 17
<211> LENGTH: 25
<212> TYPE: DNA
<213> ORGANISM: artificial sequence
<220> FEATURE:
<223> OTHER INFORMATION: synthetic oligonucleotide

<400> SEQUENCE: 17
```

```
cagaacatta actgggattt gagag                                              25

<210> SEQ ID NO 18
<211> LENGTH: 24
<212> TYPE: DNA
<213> ORGANISM: artificial sequence
<220> FEATURE:
<223> OTHER INFORMATION: synthetic oligonucleotide

<400> SEQUENCE: 18
ctccatttgc tgcattgatc tact                                               24

<210> SEQ ID NO 19
<211> LENGTH: 18
<212> TYPE: DNA
<213> ORGANISM: Artificial sequence
<220> FEATURE:
<223> OTHER INFORMATION: synthetic oligonucleotide

<400> SEQUENCE: 19
acttatgctt ccggcgta                                                      18

<210> SEQ ID NO 20
<211> LENGTH: 18
<212> TYPE: DNA
<213> ORGANISM: artificial sequence
<220> FEATURE:
<223> OTHER INFORMATION: synthetic oligonucleotide

<400> SEQUENCE: 20
gcaccagggc attcacca                                                      18

<210> SEQ ID NO 21
<211> LENGTH: 21
<212> TYPE: DNA
<213> ORGANISM: artificial sequence
<220> FEATURE:
<223> OTHER INFORMATION: synthetic oligonucleotide

<400> SEQUENCE: 21
gggaaaacgg gtttggttgg g                                                  21

<210> SEQ ID NO 22
<211> LENGTH: 25
<212> TYPE: DNA
<213> ORGANISM: artificial sequence
<220> FEATURE:
<223> OTHER INFORMATION: synthetic oligonucleotide

<400> SEQUENCE: 22
cgtcaaagtc aaactcgccg aattc                                              25

<210> SEQ ID NO 23
<211> LENGTH: 20
<212> TYPE: DNA
<213> ORGANISM: artificial sequence
<220> FEATURE:
<223> OTHER INFORMATION: synthetic oligonucleotide

<400> SEQUENCE: 23
tgccattctc cgtcttgact                                                    20

<210> SEQ ID NO 24
<211> LENGTH: 20
<212> TYPE: DNA
```

```
<213> ORGANISM: artificial sequence
<220> FEATURE:
<223> OTHER INFORMATION: synthetic oligonucleotide

<400> SEQUENCE: 24
tgcagtctcg agttcctgtt                                              20
```

METHODS FOR INDUCING RESISTANCE TO VIRUS IN A PLANT, PRIMING A PLANT TO RESIST VIRUSES, DECREASING VIRUS ACCUMULATION, OR INCREASING PR1 EXPRESSION IN A PLANT

FIELD OF THE INVENTION

The present disclosure generally relates to a microorganism and component priming plant resistant to viruses. Particularly, the present disclosure relates to fungi, a culture filtrate thereof and a polysaccharide and their applications in inducing or priming plant resistance to viruses.

The instant application contains a Sequence Listing which has been submitted electronically in ASCII format and is hereby incorporated by reference in its entirety. Said ASCII copy, created on Sep. 3, 2019, is named G4590-05400_SeqListing.txt and is 5 KB in size.

BACKGROUND OF THE INVENTION

Viruses cause serious diseases in crops, and the lost yield is estimated to total more than $30 billion annually. However, because viruses are intracellular parasites, cost-effective elimination of viruses from infected plants is difficult. Currently, no curative viricides are available for plant viral disease management. Thus, unlike other pests, if viruses can evade preventive control measures and infect plants, roguing is the main option for farmers to prevent further spread of viral disease. Traditional resistance breeding, use of pesticides to control viral vectors, and transgenic approaches to control viral diseases in crops often come at the cost of time, compromised flavor, hazardous concerns to the environment and health, as well as issues associated with genetically modified foods. One way to alleviate this problem is to induce a plant immune response to defend against virus infection.

Plants protect against pest attack by structural barriers or preexisting pest-toxic chemicals. In addition, plants have evolved a complex immune response that can ward off attack by most microbes. Plants can recognize microbe/pathogen-conserved molecular structures termed microb/pathogen-associated molecular patterns (MAMPs/PAMPs) and induce an immune response. An example of MAMPs/PAMPs are bacterial flagellin, chitin or different glucans that constitute fungal and oomycete cell walls. In addition to MAMPs/PAMPs, host-derived molecules may be generated during attacks by microbes/pathogens through lytic enzymes or mechanical forces. Some of these molecules may serve as elicitors of a plant defense response. These molecules are termed danger- or damage-associated molecular patterns (DAMPs). MAMPs and DAMPs are detected/perceived by membrane-localized pattern recognition receptors (PRRs) and induce a diverse array of defense responses commonly referred to as pattern-triggered immunity (PTI). PTI can defend against most pathogen infection; however, some plant pathogens have evolved effectors that are injected into the host cells to compromise PTI. To defend against pathogens armed with an effector, plants have evolved resistance (R) proteins to detect these effectors and induce a stronger defense response, termed effector-triggered immunity (ETI). ETI usually triggers programmed cell death at the site of infection to prevent further spreading of invasive pathogens. Both PTI and ETI are coordinated by phytohormones, such as salicylic acid (SA), jasmonic acid (JA), ethylene (ET) and abscisic acid (Pieterse, C. M., Van der Does, D., Zamioudis, C., Leon-Reyes, A., and Van Wees, S. C. 2012. *Hormonal modulation of plant immunity. Annual review of cell and developmental biology* 28:489-521). The coordination between these hormones activates a specific immune response under PTI and ETI to protect against a particular pathogen (Pieterse, C. M., Van der Does, D., Zamioudis, C., Leon-Reyes, A., and Van Wees, S. C. 2012. *Hormonal modulation of plant immunity. Annual review of cell and developmental biology* 28:489-521).

SUMMARY OF THE INVENTION

The present disclosure provides, in one aspect, culture filtrates derived from soil microorganisms to induce effective plant defense against viruses. In one embodiment, the present disclosure obtains a culture filtrate derived from *Trichosporon* sp. (F8-culture filtrate) that is much better than SA in inducing plant resistance to different viruses but without a fitness cost. The present disclosure also identifies the specific mode of action of the F8-culture filtrate, which induced an unusual priming of SA-governed responsive genes, as well as the active component of F8-culture filtrate. The finding in the present disclosure reveals an effective way for inducing plant resistance against viruses. Furthermore, the present disclosure uncovers several unusual features, which provide important knowledge for further application of induced resistance against virus infection.

In one aspect, the present disclosure provides a biologically pure culture filtrate derived from fungi, which comprises a polysaccharide comprising D-mannose, D-galactose and D-glucose with a 1,4-glucan linkage.

In one aspect, the present disclosure provides a polysaccharide comprising D-mannose, D-galactose and D-glucose with a 1,4-glucan linkage.

In one aspect, the present disclosure provides a composition comprising a culture filtrate or a polysaccharide of the present disclosure.

In another aspect, the present disclosure provides a method for inducing resistance to virus in plant or priming plant resistant to viruses, comprising treating the plant with a biologically pure culture filtrate derived from fungi or a polysaccharide comprising D-mannose, D-galactose and D-glucose with a 1,4-glucan linkage.

In another aspect, the present disclosure provides a method for decreasing virus accumulation in a plant, comprising treating the plant with a biologically pure culture filtrate derived from fungi or a polysaccharide comprising D-mannose, D-galactose and D-glucose with a 1,4-glucan linkage.

In a further aspect, the present disclosure provides a method for increasing PR1 expression in a plant, comprising treating the plant with a biologically pure culture filtrate derived from fungi or a polysaccharide comprising D-mannose, D-galactose and D-glucose with a 1,4-glucan linkage.

In some embodiment, the fungi is *Trichosporon* sp. Certain embodiment of the *Trichosporon* sp. includes *Trichosporon scarabaeorum*.

In one embodiment, the D-mannose, D-galactose and D-glucose has a α-1,4-glucan linkage; further embodiment is α-D-1,4-glucan linkage. In further embodiment, the D-mannose, D-galactose and D-glucose in the ratio about 0.5 to about 1.5:about 0.8 to about 2.0:about 8.0 to about 12.0. Certain embodiment includes that the D-mannose, D-galactose and D-glucose in the ratio about 1.0:about 1.2:about 10.0.

In one embodiment, the culture filtrate and the method do not induce canonical SAR.

Certain embodiments of the plant include, but are not limited to, Nicotiana or Brassica. In some embodiment, the Nicotiana is N. glutinosa or N. benthamiana and the Brassica is B. juncea.

In one embodiment, the virus is Tobacco mosaic virus.

BRIEF DESCRIPTION OF THE DRAWING

The patent or application file contains at least one drawing executed in color. Copies of this patent or patent application publication with color drawing(s) will be provided by the Office upon request and payment of the necessary fee.

FIG. 1A to FIG. 1D show lesion number and symptoms induced by Tobacco mosaic virus (TMV) with F2- and F8-culture filtrate pretreatment. (FIG. 1A) Nicotiana glutinosa was pretreated with $H_2O$, 5 mM salicylic acid (SA), vegetable broth (VB), or F2- and F8-culture filtrate for total of three times with a 24-h interval between each spray. Pretreated plants were inoculated with TMV at 24 hpt, and untreated plants were inoculated with buffer (mock) for a control. Photos were taken at 5 dpi. (FIG. 1B) Lesion numbers induced by TMV recorded at 5 dpi. Data are mean+SD from three plants. Different letters above the bars represent significant differences among groups, P<0.05 by one-way ANOVA with Tukey's post-test. Experiments were repeated three times with similar results. (FIG. 1C) *N. benthamiana* was pretreated with $H_2O$, 5 mM SA, VB, F2- or F8-culture filtrate for total of three times with a 24-h interval between each spray. All pretreated plants were inoculated with TMV at 24 hpt. Photos of TMV inoculated plants were taken at 7 dpi. (FIG. 1D) The level of disease index induced by TMV was recorded at 7 dpi. Box plots represent medians, 25-75 percentiles (boxes), and minimum and maximum values (whiskers) from 6 plants. Different letters above the bars represent significant differences among groups, P<0.05 by one-way ANOVA with Tukey's post-test. Experiments were repeated three times with similar results.

FIG. 2A and Figure B show lesion number on F8-culture filtrate treated *Nicotiana glutinosa* inoculated with purified Tobacco mosaic virus (TMV) particle. (FIG. 2A) *N. glutinosa* was pretreated with $H_2O$, 5 mM salicylic acid (SA), vegetable broth (VB) and F8-culture filtrate for total of three times with a 24-h interval between each spray. Pretreated plants were inoculated with 1 μg/ml, 10 μg/ml and 50 μg/ml of TMV particles, respectively at 24 hpt, and untreated plants were inoculated with buffer (mock) for a control. Photos were taken at 5 dpi. (FIG. 2B) Lesion numbers induced by TMV particle was recorded at 5 dpi. UC, uncountable. Data are mean+SD from three plants. Different letters above the bars represent significant differences among groups, P<0.05 by one-way ANOVA with Tukey's post-test. Different letters above the bars represent significant differences among groups, P<0.05 by one-way ANOVA with Tukey's post-test.

FIG. 3A and FIG. 3B show symptom on F8-culture filtrate treated *Nicotiana benthamiana* inoculated with purified Tobacco mosaic virus (TMV) particle. (FIG. 3A) *N. benthamiana* was pretreated with $H_2O$, 5 mM salicylic acid (SA), VB or F8-culture filtrate (F8) three times at 24-h intervals. All plants were inoculated with 1 μg/ml, 10 μg/ml or 50 μg/ml of TMV particles at 24 hpt. The photo was taken at 5 dpi. (FIG. 3B) The level of disease index induced by TMV was recorded at 5 dpi. Box plots represent medians, 25-75 percentiles (boxes), and minimum and maximum values (whiskers) from six plants. Different letters above the bars represent significant differences among groups, P<0.05 by one-way ANOVA with Tukey's post-test.

FIGS. 4A to 4F show that F8-culture filtrate does not confer systemic protection against Tobacco mosaic virus (TMV) or conical systemic acquired resistance (SAR) in *Nicotiana benthamiana*. The lower three leaves (local) of *N. benthamiana* were pretreated with $H_2O$ ($H_2O^L$), 5 mM salicylic acid ($SA^L$), vegetable broth ($VB^L$) or F8-culture filtrate ($F8^L$) for total of three times with a 24-h interval between each spray. The three upper leaves (systemic) were inoculated with TMV at 2 dpt. Whole plants treated with F8-culture filtrate (F8) for total of three times with a 24-h interval between each spray was used as control. The photo was taken at 7 dpi (FIG. 4A), and the level of disease induced by TMV was recorded (FIG. 4B). Box plots represent medians, 25-75 percentiles (boxes), and minimum and maximum values (whiskers) from five plants. Different letters above the bars represent significant differences among groups, P<0.05 by one-way ANOVA with Tukey's post-test. Experiments were repeated at least three times with similar results. For expression analysis of SAR marker gene PR-1, local leaves of plants were pretreated with $H_2O$, 5 mM SA, VB or F8-culture filtrate (F8) for total of three times with a 24-h interval between each spray. After treatment, local leaves (FIG. 4C) and systemic leaves (FIG. 4D) were collected at 24 hpt. Whole plants treated with $H_2O$, 5 mM SA, VB or F8-culture filtrate (F8) were controls. The relative expression of PR-1 was detected by qRT-PCR. Data are mean+SD from three plants. Student's t test was used to analyzed the data between indicated treatment and $H_2O$-pretreated control group. Asterisks indicate significant differences between $H_2O$ or F8 treated plants (*P<0.05, P<0.01); ns, not significant. Experiments were repeated at least three times with similar results. (FIG. 4**E) The whole plant was pretreated with $H_2O$, 5 mM SA, VB or F8-culture filtrate (F8) for total of three times with a 24-h interval between each spray. Leaves were collected at 24 hpt. The relative expression of PR-1 was detected by qRT-PCR. Data are mean+SD from three plants. Student's t test was used to analyzed the data between indicated treatment and $H_2O$-pretreated control group. Asterisks indicate significant differences between $H_2O$ or F8 treated plants (*P<0.05, **P<0.01); ns, not significant. Experiments were repeated at least three times with similar results. The whole plant was pretreated with $H_2O$ or F8-culture filtrate (F8) for total of three times with a 24-h interval between each spray. Pretreated plants were inoculated with TMV at 24 hpt. Inoculated leaves were collected at 24 hpi, 48 hpi, 72 hpi and 96 hpi. The relative expression of PR-1 was detected by qRT-PCR. Data are mean+SD from three to five plants. Asterisks indicate significant differences between $H_2O$ or F8 treated plants (*P<0.05, P<0.01); ns, not significant. (FIG. 4**F) The whole plant was pretreated with $H_2O$ or F8-culture filtrate (F8) for total of three times with a 24-h interval between each spray. Pretreated plants were inoculated with TMV at 24 hpt. Inoculated leaves were collected at 24 hpi, 48 hpi, 72 hpi and 96 hpi. The relative expression of PR-1 was detected by qRT-PCR. Data are mean+SD from three to five plants. Student's t test was used to analyzed the data between F8 treatment and $H_2O$-pretreated control group. Asterisks indicate significant differences between $H_2O$ or F8 treated plants (*P<0.05, **P<0.01); ns, not significant.

FIG. 5A to FIG. 5F show *Nicotiana benthamiana* infected with TMV tagged with green fluorescence protein (TMV-GFP). (FIG. 5A) *N. benthamiana* was pretreated with $H_2O$, 5 mM salicylic acid (SA), VB or F8-culture filtrate (F8) for total of three times with a 24-h interval between each spray.

All plants were inoculated with TMV-GFP at 24 hpt. Photos were taken under UV light at 5 and 7 dpi. Scale bar=2 cm.

FIG. 6A to FIG. 6D show symptoms induced by Turnip mosaic virus (TuMV) in Brassica juncea pretreated with F8-culture filtrate and fitness cost analysis of Nicotiana benthamiana and Brassica juncea with F8-culture filtrate pretreatment. (FIG. 6A) Brassica juncea was pretreated with $H_2O$, VB or F8-culture filtrate (F8) for total of three times with a 24-h interval between each spray, then inoculated with TuMV at 24 hpt. Photos were taken at 13 dpi. Scale bar=5 cm. (FIG. 6B) The disease index induced by TuMV was recorded at 13 dpi. Box plots represent medians, 25-75 percentiles (boxes), and minimum and maximum values (whiskers) from six plants. Different letters above the bars represent significant differences among groups, P<0.05 by one-way ANOVA with Tukey's post-test. Experiments were repeated three times with similar results. Shoots of 6 N. benthamiana (15 days after seeding) (FIG. 6C) or Brssica juncea (10 days after seeding) (FIG. 6D) without treatment (WO) or with F8-culture filtrate (F8) pretreatment were used to measure fresh weight and leaf area at 20 or 25 dpt, respectively. All leaves were photographed with identical illumination and exposure conditions. The average leaf area per plant was calculated.

(FIG. 7C) F8 fungi was cultured on 10% V-8 agar plate (V-8) and potato dextrose agar plate (PDA) for 15 days at 25° C. Colony morphology was photographed and presented with front and back side. Microscopy depicting the morphology of arthroconidia and hyphae of F8 fungi grown on V-8 plate, 25° C., for 7 days. Scale bar=20 μm.

FIG. 8A to FIG. 8F show fractionation of F8-culture for antiviral activity analysis, and identification, NMR and linkage analysis of active functional compound derived from F8-culture filtrate. Nicotiana benthamiana was pretreated with $H_2O$, 5 mM salicylic acid (SA), VB, F8-culture filtrate (F8), F8-sephadex fraction 2 (F8-fr2), $H_2O$-re-suspended pellets derived from F8-fr2 precipitated with 20%, 50% and 80% ethanol (F8-fr2-20, 50 and 80% EtOH ppt) and HPLC-purified peaks 1 to 3 (*1 to *3) from $H_2O$-re-suspended F8-fr2-80% EtOH ppt for total of three times with a 24-h interval between each spray. We define peak *2 as F8-polysaccharide. Pretreated plants were inoculated with TMV at 24 hpt. (FIG. 8A) Photos of Tobacco mosaic virus (TMV) inoculated plants taken at 7 dpi. (FIG. 8B) The disease index induced by TMV was recorded at 7 dpi. Box plots represent medians, 25-75 percentiles (boxes), and minimum and maximum values (whiskers) from six plants. Different letters above the bars represent significant differences among groups, P<0.05 by one-way ANOVA with Tukey's post-test. Experiments were repeated three times with similar results. (FIG. 8C) MALDI-TOF mass spectra of F8-sephadex fraction 2 (F8-fr2), $H_2O$-re-suspended pellets derived from F8-fr2 precipitated with 20%, 50% and 80% ethanol (F8-fr2-20, 50 and 80% EtOH ppt) and HPLC-purified peaks 1 to 3 (*1 to *3) from $H_2O$ re-suspended F8-fr2-80% EtOH ppt at m/z 1800-6000, where the most peaks are. (FIG. 8D) HPLC-ELSD profile of F8-fr2-80% EtOH ppt. Three major peaks, *1 to *3, were collected for MALDI-TOF mass spectra analysis in (C). *2 was defined to be F8-polysaccharide. (FIG. 8E) Heteronuclear Single Quantum Coherence spectrum ($^1H$-$^{13}C$ HSQC, D20, 323K, 600 MHz) of F8-polysaccharide. Determination of the $^1J_{HC}$ of G1 (alpha configuration) was based on the satellite signals of G1 (dH 5.63, dc 99.9) in the Heteronuclear Multiple Bond Correlation spectrum ($^1H$-$^{13}C$ HMBC). (FIG. 8F) Gas chromatography mass spectrometry (GC-MS) linkage analysis of F8-polysaccharide. 1,4-linked-D-glucopyranosyl residue was the main linkage composition.

FIG. 9A to FIG. 9D show the relative expression of salicylic acid (SA) associated immune marker genes. The relative expression of SA-responsive genes PR-1 (FIG. 9A) and PR-2 (FIG. 9C) detected by qRT-PCR. Plants were pretreated with $H_2O$ or F8-polysaccharide for total of three times with a 24-h interval between each spray, then samples collected at 0, 12, 24, 36, 48, 72, 96 hpt. Tobacco mosaic virus (TMV) inoculation or mock treatment was conducted on different indicated 24 hpt plants (FIG. 9B, FIG. 9D). Leaf samples were collected from TMV-infected plants at 1-, 36-, 48- and 72-h post TMV inoculation. The relative expression of PR-1 (FIG. 9B) and PR-2 (FIG. 9D) was detected by qRT-PCR. Data are mean+SD from three to five plants. All lettering indicates statistically significance (P<0.05 by one-way ANOVA with Tukey's post-test). "a" indicates statistically significance between F8-polysaccharide-treated samples at indicated time to F8-polysaccharide-treated samples collected at 0 hpt. "b" indicates statistically significant between $H_2O$ and F8-polysaccharide-treated samples at each time course. "c" indicates statistically significance between $H_2O$-treated mock-inoculated and F8-treated mock-inoculated. "d" indicates statistically significance between $H_2O$-treated TMV-inoculated and F8-treated TMV-inoculated. "e" indicates statistically significance between $H_2O$-treated mock-inoculated and $H_2O$-treated TMV-inoculated. "f" indicates statistically significance between F8-treated mock-inoculated and F8-treated TMV-inoculated. "g" indicates statistically significance to $H_2O$-treated mock-inoculated at 0 hpi.

FIG. 11A and FIG. 11B show symptoms induced by TMV in *N. benthamiana* with F8-culture filtrate and pellet pretreatment. (FIG. 11A) *N. benthamiana* was pretreated with $H_2O$, 5 mM salicylic acid (SA), VB, F8-culture filtrate (F8), F8-derived pellet (F8-pellet) or 2-fold F8-derived pellet (2*F8-pellet) three times at 24-h intervals. All plants were inoculated with TMV at 24 hpt. The photo was taken at 7 dpi. (FIG. 11B) The level of disease index induced by TMV was recorded at 7 dpi. Box plots represent medians, 25-75 percentiles (boxes), and minimum and maximum values (whiskers) from six plants. Different letters above the bars represent significant differences among groups, P<0.05 by one-way ANOVA with Tukey's post-test. Experiments were repeated at least three times with similar results.

FIG. 12A to FIG. 12D show analysis of fractions derived from fractionation of F8-cluture filtrate on inducing plant resistance against TMV. F8-culture filtrate was passed through a Sephadex LH2O column, and 8 fractions (F8-fr1 to -fr8) were collected. *Nicotiana glutinosa* (FIG. 12A) and *N. benthamiana* (FIG. 12B and FIG. 12C) were pretreated with $H_2O$, 5 mM SA, VB, F8-culture filtrate (F8) or F8-culture filtrate fractions F8-fr1-8 three times at 24-h intervals. Pretreated plants were inoculated with TMV at 24 hpt. Lesion numbers induced by TMV on *N. glutinosa* were recorded at 5 dpi. Data are mean+SD from three plants. Different letters above the bars represent significant differences among groups, P<0.05 by one-way ANOVA with Tukey's post-test. Experiments were repeated three times with similar results. The level of disease induced by TMV on *N. benthamiana* was recorded at 7 dpi. Only fractions F8-fr1-4 are shown here. Box plots represent medians, 25-75 percentiles (boxes), and minimum and maximum values (whiskers) from six plants. The different letters above the bars represent significant differences among groups, P<0.05 by one-way ANOVA with Tukey's post-test. Experiments were repeated three times with similar results. (FIG. 12D) MALDI-TOF mass spectra of F8-fr1-8 at m/z 1000-5000, area with the most peaks.

FIG. 14A to FIG. 14D show the relative expression of immune marker genes. (FIG. 14A) Plants were pretreated with 5 mM salicylic acid (SA), 250 μM methyl jasmonate (Me-JA) or 2 mM 1-aminocyclopropane-1-carboxylic acid (ACC). Leaves were collected at the indicated time. The relative expression of SA-responsive genes PR-1 and PR-2, jasmonic acid (JA)-responsive genes plant defensin 1.2 (PDF-1.2) and PR-4, and ethylene (ET)-responsive genes osmotin (OSM) and ethylene-responsive element binding proteins (EREBP) were detected by qRT-PCR. Plants were pretreated with $H_2O$ or F8-polysaccharide for total of three times with a 24-h interval between each spray, then collected at 0, 12 and 24 hpt. At 24 hpt, Tobacco mosaic virus (TMV) was inoculated into treated plants, and leaf samples were collected from TMV-infected plants at 12, 24, 48 and 72-h post TMV inoculation. The TMV-CP was quantified by qRT-PCR (FIG. 14B). The relative expression of PDF1.2 (FIG. 14C) and EREBP (FIG. 14D) was detected by qRT-PCR from TMV-infected plants at 1, 12, 24, 48 and 72-h post TMV inoculation that were pretreated with $H_2O$ or F8-polysaccharide. Data are mean+SD from three plants. All $H_2O$-treated samples are compared to $H_2O$-treated samples collected at 0 hpt and "a" indicates statistically significant (P<0.05 by one-way ANOVA with Tukey's post-test). All F8-polysaccharide-treated samples are compared to F8-polysaccharide-treated samples collected at 0 hpt and "b" indicates statistically significant (P<0.05 by one-way ANOVA with Tukey's post-test). $H_2O$ and F8-polysaccharide-treated samples were compared at each time course, and "c" indicates statistically significant (P<0.05). N. D., not detected.

FIG. 15A and FIG. 15B show disease index of *N. benthamiana* inoculated with TMV and *Brassica juncea* inoculated with TuMV. (FIG. 15A) *N. benthamiana* were inoculated with TMV. The disease index was classified into 4 levels according to the degree of yellowing, stunting and wilting at 7 dpi. (FIG. 15B) *Brassica juncea* were inoculated with TuMV. The disease index was classified into 3 levels according to the degree of leaf mosaic and stunting at 13 dpi.

DETAILED DESCRIPTION OF THE INVENTION

Figure 5:
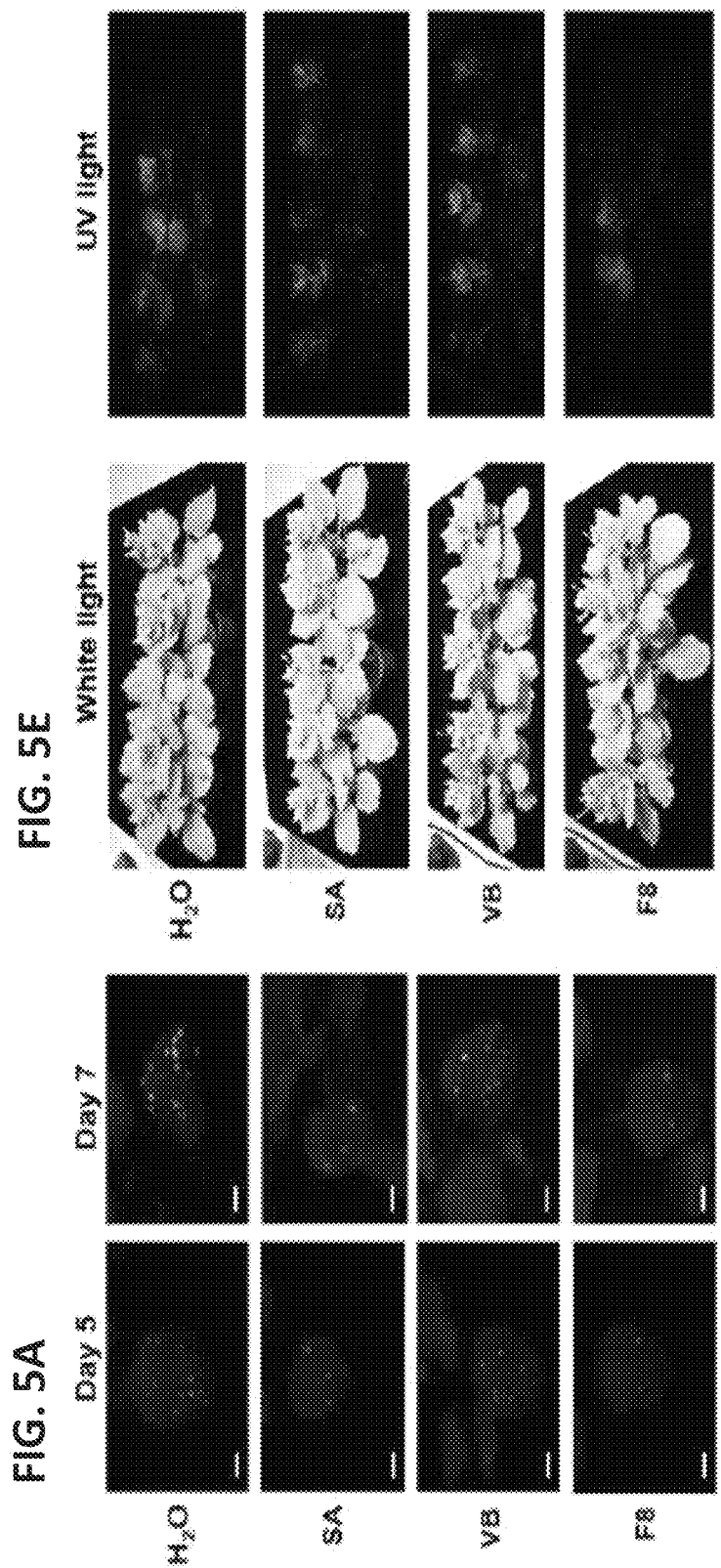
(FIG. 5B) The mean number of TMV-GFP infection foci per plant at 5 dpi. Data are mean+SD from two to five plants. Different letters above the bars represent significant differences among groups, P<0.05 by one-way ANOVA with Tukey's post-test.
(FIG. 5C) The relative accumulation of TMV-GFP per foci. TMV-GFP was quantified by qRT-PCR, and β-actin was an internal control. Data are mean+SD from two to five plants. Different letters above the bars represent significant differences among groups, P<0.05 by one-way ANOVA with Tukey's post-test.
(FIG. 5D) The area (mm$^2$) of TMV-GFP infection foci was measured at 5 and 7 dpi.
FIG. 5E) Photos of TMV-GFP-infected plants taken under white light or UV light at 13 dpi.
(FIG. 5F) The mean time (days) for TMV-GFP to move to apical leaves. Experiments were repeated at least three times with similar results. Data are mean+SD from two to five plants.

When the articles "a," "an," "one," "the," and "said" are used herein, the mean "at least one" or "one or more" unless otherwise indicated.

As used herein, a "biologically pure fungi culture" refers to a culture of fungi containing no other fungi or bacterial species in quantities sufficient to interfere with the replication of the culture or be detected by normal techniques.

As used herin, the terms "agriculturally acceptable carrier" and "carrier" are interchangeable.

As used herein, the terms "composition" and "formulation" are interchangeable throughout the application.

As used herein, the term "effective amount" refers to a quantity which is sufficient to prime a statistically significant resistance to viruses in a plant as compared to the control-treated plant.

Plant viruses cause devastating diseases in plants, yet not effective viricide is available for agricultural application. In plants, local infection may also induce a systemic plant immune response. Two types of induced systemic immune responses, systemic acquired response (SAR) and induced systemic response (ISR), have been reported in plants (Pieterse, C. M., Zamioudis, C., Berendsen, R. L., Weller, D. M., Van Wees, S. C., and Bakker, P. A. 2014. *Induced systemic resistance by beneficial microbes. Annual review of phytopathology* 52:347-375). ISR is induced by plant growth-promoting rhizobacteria (PGPR) and depends on JA and ET (Pieterse, C. M., Zamioudis, C., Berendsen, R. L., Weller, D. M., Van Wees, S. C., and Bakker, P. A. 2014. *Induced systemic resistance by beneficial microbes. Annual review of phytopathology* 52:347-375). The onset of SAR depends on SA, and SAR is efficient against a broad spectrum of pathogens including viruses. SAR is usually induced by pathogens that cause a necrotic lesion resulting from a hypersensitive response during an incompatible interaction or cell death with a compatible interaction.

The systemic immune response is usually associated with a primed state, whereby plants respond faster and/or more strongly in activating defense responses when subsequently challenged by pathogens (Mauch-Mani, B., Baccelli, I., Luna, E., and Flors, V. 2017. *Defense Priming: An Adaptive Part of Induced Resistance. Annual review of plant biology* 68:485-512). Elevated levels of pattern recognition receptors, dormant signaling enzymes, transcription factors, and alterations in chromatin state have been suggested to provide plants with a memory to establish a defense primed state (Mauch-Mani, B., Baccelli, I., Luna, E., and Flors, V. 2017. *Defense Priming: An Adaptive Part of Induced Resistance. Annual review of plant biology* 68:485-512). The immune priming allows plants to better defend against pathogen invasion with lower resistance-associated fitness cost (Mauch-Mani, B., Baccelli, I., Luna, E., and Flors, V. 2017. *Defense Priming: An Adaptive Part of Induced Resistance. Annual review of plant biology* 68: 485-512).

Viruses usually trigger the SA-related plant defense response, and exogenous application of SA or its analogs such as benzo-thiadiazol-7-carbothioic acid-S-methyl ester (BTH) and acibenzolar-S-methyl (a derivative of BTH) can trigger the SAR against virus infection. However, effectiveness and phytotoxicity hamper the application of SA or its analogs in the field.

The present disclosure provides a culture filtrate, filtrate fractations and polysaccharides derived from fungi that enhance plant viral resistance. In an embodiment, a cultured filtrate, designated F8-culture filtrate, derived from a fungus belonging to the genus *Trichosporon*, induced strong resistance to various viruses on different plants. In some embodiments, the infection rate of TMV-inoculated *N. benthamiana* with F8-culture filtrate pretreatment may decrease to 0%, whereas salicylic acid (SA) pretreated *N. benthamiana* attenuated TMV caused symptoms, but remained 100% infected. Notably, F8-culture filtrate only triggered local defense, but was much more effective than conventional SA-mediated systematic acquired resistance. Our finding revealed that microbial cultured metabolites provided a rich source for identification of potent elicitors in plant defense.

From the culture filtrate, a previously unknown polysaccharide is identified, which comprises D-mannose, D-galactose and D-glucose with a 1,4-glucan linkage to be responsible for the induction of plant resistance against viruses through priming of SA-governed immune responsive genes.

The culture filtrate is derived from fungi, comprising a polysaccharide comprising D-mannose, D-galactose and D-glucose with a 1,4-glucan linkage. Preferably, the linkage isa-1,4-glucan linkage; more preferably, the linkage isa-D-1,4-glucan linkage.

The D-mannose, D-galactose and D-glucose in the ratio about 0.5 to about 1.5:about 0.8 to about 2.0:about 8.0 to 12.0. Preferably, the D-mannose, D-galactose and D-glucose in the ratio about 1.0:about 1.2:about 10.0.

Examples of the fungi include, but are not limited to, *Trichosporon* sp. Certain embodiment of the *Trichosporon* sp. includes *Trichosporon scarabaeorum*.

The present disclosure also provides a composition comprising a culture filtrate or a polysaccharide of the present disclosure.

Accordingly, the fungi, the culture filtrate and the polysaccharide of the present disclosure can induce resistance to virus in plant or prime plant resistant to viruses, comprising treating the plant with a biologically pure culture filtrate derived from fungi or a polysaccharide comprising D-mannose, D-galactose and D-glucose with a 1,4-glucan linkage.

Alternatively, the fungi, the culture filtrate and the polysaccharide of the present disclosure can decrease virus accumulation in a plant, comprising treating the plant with a biologically pure culture filtrate derived from fungi or a polysaccharide comprising D-mannose, D-galactose and D-glucose with a 1,4-glucan linkage.

Alternatively, the fungi, the culture filtrate and the polysaccharide of the present disclosure can increase PR1 expression in a plant, comprising treating the plant with a biologically pure culture filtrate derived from fungi or a polysaccharide comprising D-mannose, D-galactose and D-glucose with a 1,4-glucan linkage.

The fungi, the culture filtrate and the polysaccharide of the present disclosure do not induce canonical SAR.

Certain embodiments of the plant include, but are not limited to, *Nicotiana* or *Brassica*. In some embodiment, the *Nicotiana* is *N. glutinosa* or *N. benthamiana* and the *Brassica* is *B. juncea*.

The virus to be resisted includes, but is not limited to, Tobacco mosaic virus.

In addition to one or more biologically pure culture filtrates as described in the present disclosure, the composition also comprises an agriculturally acceptable carrier. The carrier can include a dispersant, a surfactant, an additive, water, a thickener, an anti-caking agent, residue breakdown, a composting formulation, a granular application, diatomaceous earth, an oil, a coloring agent, a stabilizer, a preservative, a polymer, a coating, or a combination thereof. One of ordinary skill in the art can readily determine the appropriate carrier to be used taking into consideration factors such as a particular fungi strain, plant to which the composition is to be applied, type of soil, climate conditions, whether the composition is in liquid, solid or powder form, and the like.

The additive can comprise an oil, a gum, a resin, a clay, a polyoxyethylene glycol, a terpene, a viscid organic, a fatty acid ester, a sulfated alcohol, an alkyl sulfonate, a petroleum sulfonate, an alcohol sulfate, a sodium alkyl butane diamate, a polyester of sodium thiobutant dioate, a benzene acetonitrile derivative, a proteinaceous material, or a combination thereof. The proteinaceous material can include a milk product, wheat flour, soybean meal, blood, albumin, gelatin, or a combination thereof. The thickener can comprise a long chain alkylsulfonate of polyethylene glycol, polyoxyethylene oleate, or a combination thereof. The surfactant can contain a heavy petroleum oil, a heavy petroleum distillate, a polyol fatty acid ester, a polyethoxylated fatty acid ester, an aryl alkyl polyoxyethylene glycol, an alkyl amine acetate, an alkyl aryl sulfonate, a polyhydric alcohol, an alkyl phosphate, or a combination thereof. The anti-caking agent can include a sodium salt such as a sodium sulfite, a sodium sulfate, a sodium salt of monomethyl naphthalene sulfonate, a sodium salt of dimethyl naphthalene sulfonate, or a combination thereof; or a calcium salt such as calcium carbonate, diatomaceous earth, or a combination thereof.

Any agriculturally acceptable carrier can be used. Such carriers include, but are not limited to, vermiculite, charcoal, sugar factory carbonation press mud, rice husk, carboxymethyl cellulose, peat, perlite, fine sand, calcium carbonate, flour, alum, a starch, talc, polyvinyl pyrrolidone, or a combination thereof.

Compositions can be prepared as solid, liquid or powdered formulations as is known in the art. When the composition is prepared as a liquid formulation for application to plants or to a plant growth medium, it can be prepared in a concentrated formulation or a working form formulation. When the composition is prepared as a solid formulation for application to plants or to a plant growth medium, it can be prepared as a granular formulation or a powder agent.

The following non-limiting examples illustrate various aspects of the present invention.

EXAMPLES

Material and Methods

Isolation of soil microorganisms and preparation of culture filtrate for antiviral activity assay.

Soil samples (10-20 g) were collected from 5-10 cm depth in Taipei, Taiwan. Soil micoorganisms were isolated with selective medium as reported by Ko et al. (2010), except we adjusted the pH of vegetable broth (VB) to 4.7 for culture of F8 fungi and the VB was filtrated through a 25-µm filter before storing at −80° C.

Plant Materials and Inoculation of Viruses

Plants were grown in a growth chamber with 10,000 lux fluorescent light and a 16-h light/8-h dark cycle. *N. glutinosa* (6-7 weeks old, 8-10 leaf stage), *N. benthamiana* (3-4 weeks old, 5-6 leaf stage) and *Brassica juncea* (14 days old, 2-3 true-leaf stage) were used for treatment and/or inoculation. For virus inoculation, plants were dusted with 600-grit silicon carbide powder (Sigma-Aldrich, St. Louis, Mo., USA) and mechanically inoculated. Virus inoculum was prepared with 100 ml of 0.1 M potassium phosphate (KP) buffer (61.5% of 0.1 M $K_2HPO_4$ and 38.5% 0.1 M $KH_2PO_4$, pH 7.0) mixed with 0.1 g of lyophilized leaves of plants infected with Tobacco mosaic virus (TMV) (FIGS. 1, 4A-E, 8 and 9; FIG. 10, 11, 12, 14 and 15; Table 1), or TMV tagged with green fluorescence protein (TMV-GFP) (FIG. 5) (Rabindran, S., and Dawson, W.O. 2001. *Assessment of recombinants that arise from the use of a TMV-based transient expression vector. Virology* 284:182-189). Different concentrations of TMV purified particle inoculum was diluted with 0.1 M potassium phosphate (KP) buffer (61.5% of 0.1 M K2HPO4 and 38.5% 0.1 M $KH_2PO_4$, pH 7.0) (FIGS. 2, 3, and 4F; Table 2). Turnip mosaic virus (TuMV) inoculum was prepared with 0.1 g of fresh leaves from plants infected with TuMV ground with 10 ml of 0.1 M sodium phosphate buffer (0.1 M NaH2PO4, 0.1 M $Na2HPO_4$ and 0.5% $Na_2SO_3$, pH 7.4). The severity of TMV or TuMV symptom of infected plants were scored based on external phenotype (FIG. 15). Transmission electron microscope (Philips Electronic Instruments, Mahwah, N.J.) was used to examine TMV particles of different inoculums.

Purification of TMV Particles

Leaves of TMV-infected *N. benthamiana* were harvested approximately 5 days after inoculation. The initial purification of TMV virus particles followed the protocol as described by Gooding and Hebert (1967) with modifications. Briefly, polyethylene glycol with molecular weight 8000 (PEG 8000) (Sigma-Aldrich) was used instead of PEG 6000. In addition, the semi-purified preparation was submitted to linear density sucrose gradient (0-18%), and ultra-centrifuged at 228,000×g for 1.5 h. The light scattering region was collected and diluted with 100 ml of suspension buffer (35 mM $Na_2HPO_4$, 15 mM $NaH_2PO_4$ and 0.05% 2-mercaptoethanol, pH7.2). NaCl (0.4 g) and PEG 8000 (4 g) were added and stirred for at least 1 h on ice, then centrifuged at 9000×g for 15 min at 4° C. The pellets were re-suspended in 1 ml of suspension buffer. The concentration of the purified TMV suspension was determined (A260 nm=0.3 for 1 mg/mL of TMV) with a Nanodrop (ND-1000, Thermo Fisher Scientific, MA, USA).

Antiviral Activity Assays

Whole plants were sprayed with 0.4 ml $H_2O$, VB, culture filtrate derived from microorganism or 5 mM salicylic acid (SA, Sigma-Aldrich) for total of three times with a 24-h interval between each spray. Twenty-four hours after the final treatment, plants were rubbed with the virus inoculum.

Measurement of Area of TMV-GFP Infection Foci

Photographs of TMV-GFP fluorescent infection foci in *N. benthamiana* leaves were taken under UV light at 5 and 7 days post-inoculation (dpi), and the level of fluorescence as well as the areas of fluorescent infection sites in each leaf were measured by using ImageJ v1.47. All imaging was conducted under identical illumination and exposure conditions to allow for comparisons. Mean values of areas of all infection foci per treatment were calculated.

RNA Extraction and Gene Expression Analysis

Total RNA was isolated by use of Trizol (Invitrogen, Bethesda, Md.) according to the manufacturer's instruction. Residual DNA was removed by using the TURBO DNA-free kit (Ambion, Austin Tex., USA). cDNA was synthesized by using the PrimeScript RT-PCR Kit (Takara Bio, Shiga, Japan). Quantitative RT-PCR (qRT-PCR) involved the SYBR protocol (Life Technologies) and the ABI 7100 real-time PCR system (Applied Biosystems, Carlsbad, Calif.). For quantitative analysis, actin was used as an input control. Relative fold change in mRNA expression was determined by calculating $2^{-\Delta\Delta Ct}$. The sequences of primers used are in Table S1.

Identification of Fungi and Phylogenetic Analysis

Genomic DNA was extracted by the CTAB method (Chang et al., 1993). Internal transcribed spacer or 26S rDNA region sequences were amplified with specific primers designed for the ITS1-5.85-ITS2 region (ITS5e-F and ITS4e-R) and D1/D2 domain (LR1-F and LR3-R), respectively (Table S1). The sequence alignment involved use of CLUSTAL X (1.81) (Thompson, JD., Gibson, T. J., Plewniak, F., Jeanmougin, F., and Higgins, D. G. 1997. *The CLUSTAL_X windows interface: flexible strategies for multiple sequence alignment aided by quality analysis tools. Nucleic acids research* 25:4876-4882). All of the phylogenetic trees in this study were generated by using MEGA5 (Tamura, K., Peterson, D., Peterson, N., Stecher, G., Nei, M, and Kumar, S. 2011. *MEGA5: molecular evolutionary genetics analysis using maximum likelihood, evolutionary distance, and maximum parsimony methods. Molecular biology and evolution* 28:2731-2739). Phylogenetic analyses involved neighbor-joining (NJ) and maximum likelihood (ML) methods. The branch supports of NJ and ML methods were analyzed by using PAUP* 4.0 b 10 (Swofford, D. L. 2003. {*PAUP*. Phylogenetic Analysis Using Parsimony (*and Other Methods). Version* 4.}. Sinauer Associates) with bootstrapping. NJ involved a Kimura 2-parameter model, and node support was analyzed by bootstrapping with 1,000 replicates. ML involved a Jukes-Cantor model and bootstrapping with 1,000 replicates. Bootstrap minimal concordance was set to 80%. These sequence data have been submitted to the GenBank databases under accession number MG757354 and MG752969.

Measurement of Leaf Area and Fresh Weight

*N. benthamiana* (16 days after seeding) and *Brassica juncea* (10 days after seeding) were treated with the F8-culture filtrate as described in the antiviral activity assay. All shoot tissues of individual plants were measured for fresh weight. Leaves were randomly collected from 6 individual *N. benthamiana* or *Brassica juncea* plants with or without F8-culture filtrate treatment at 20 days or 25 days post-treatment (dpt), respectively. Photos were taken from every collected leaf by using identical illumination and exposure conditions. Each leaf area was measured by using Image J.

Identifying the Active Functional Compound of F8-Culture Filtrate for Inducing Plant Resistance To purify and characterize the active functional compound, freeze-dried powder (from 90 ml of F8-culture filtrate) was dissolved in 90 ml of distilled $H_2O$. After centrifugation at 6000×g for 10 min, the supernatant was separated on a prepacked gel filtration Sephadex LH-20 column (GE Healthcare Life Sciences, Uppsala, Sweden) eluted with 500 ml of $H_2O$ per fraction. Eight fractions derived from the F8-culture filtrate (F8-fr1-8) were collected and freeze-dried, then dissolved in 90 ml distilled $H_2O$ and tested for antiviral activity.

Isolation of Polysaccharides

The F8-fr was mixed with a ratio of ethanol to $H_2O$/ethanol [80:20 (v/v)] and stirred vigorously at 4° C. The precipitate was centrifuged at 6000×g for 10 min. The supernatant was precipitated again by the addition of a ratio of ethanol to $H_2O$/ethanol [50:50 (v/v)] and $H_2O$/ethanol [20:80 (v/v)]. All of the precipitate was dissolved in 90 ml distilled $H_2O$, then tested for antiviral activity. To remove minor impurities, the F8-fr2-80% EtOH pellets were further purified by preparative high-performance liquid chromatography (HPLC) with a TSKgel P2500GW column (21.5 mm×60 cm, Tosoh Bioscience LLC, Japan) for structure elucidation. The HPLC-purified F8-frs were dissolved in distilled $H_2O$, then tested for antiviral activity.

Polysaccharide Structure Elucidation

For sugar composition analysis, the purified polysaccharide underwent methanolysis by 3N Methanolic-HCl (Supelco) for 14 h at 85° C. in a sealed glass tube. After drying with Na, the residue was then acetylated with 50 μL acetic anhydride and 10 μL pyridine in 500 μL methanol at room temperature for 20 min. All solvent was removed by a steady stream of nitrogen, then the Sylon HTP kit (Supelco) was used for trimthylation at room temperature for 30 min. The dried sample was dissolved with 800 μL n-hexane (HPLC grade, Sigma), then analyzed by GC-MS. All data were collected by GC-MS (Bruker) with a HP-5MS silica capillary column (30 m×0.25 mm I.D., HP) and temperature gradient of 1 min at 60° C., 2 min at 60-90° C., 9 min at 90-290° C., 5 min at 290° C., 36 min at 290-300° C., and kept for 2 min at 300° C.

For the linkage analysis, the polysaccharide was lyophilized, then dissolved in 1 mL DMSO overnight at 80° C. NaOH pellets were ground with a motor and added into the sample solution for 2-h incubation in a sealed tube. The sample was methylated by using $CH_3I$ and powder NaOH in DMSO. Furthermore, the dried sample was partitioned with $H_2O$ and $CHCl_3$ to give the organic layer. The dried organic layer residue was further hydrolyzed with 2 M trifluoroacetic acid (TFA) at 120° C. for 1 h to give the partially methylated monosaccharides. Then the sample was reduced by $NaBD_4$ at room temperature for 1 h and neutralized with AcOH. The solution was co-evaporated with MeOH to remove the boric acid. After that, the sample was acetylated with 1:2 pyridine-$Ac_2O$ at 80° C. for 1 h and the mixture was partitioned with $H_2O$—$CHCl_3$. The organic layer containing methyl alditol acetates was analyzed by GC-MS on HP-5MS silica capillary column (30 m×0.25 mm I.D., HP) temperature gradient 1 min at 60° C., 2 min at 60-90° C., 9 min at 90-290° C., 5 min at 290° C., 36 min at 290-300° C., and kept for 2 min at 300° C. The polysaccharide consisted of terminal-D-glucopyranosyl residue, 4-linked-D-glucopyranosyl residue, and 4,6-linked-D-gluctopyranosyl residue.

The 1D and 2D NMR spectra were collected by using a Bruker AVANCE 600 spectrometer in $D_2O$ at 323K. All 2D NMR experiments were carried out with standard pulse sequences provided by Bruker. For the NMR data, the major composition of the polysaccharide was determined to be α-1,4-glucan. The assignments of protons and carbons of the sample are in Table 4.

TABLE 4

$^1H$ and $^{13}C$ NMR chemical shifts (δ, $D_2O$, 323K) of F8-polysaccharide

| | H-1<br>C-1 | H-2<br>C-2 | H-3<br>C-3 | H-4<br>C-4 | H-5<br>C-5 | H-6a; H-6b<br>C-6 |
|---|---|---|---|---|---|---|
| $^a$-(1→4)-α-D-Glcp-(1→4)- | 5.63<br>99.9 | 3.88<br>71.8 | 4.21<br>73.6 | 3.90<br>77.4 | 4.10<br>71.8 | 4.11; 4.08<br>60.8 |

$^a$The configuration was determined based on the $^1J_{H1-C1}$ = 173.3 Hz

MALDI-TOF MS

An amount of 1 μL sample was spotted on a MTP 384 ground steel plate and 1 μL saturated universal matrix solution (Sigma, dissolved in 50% acetonitrile with 0.1% TFA) was spotted on top of the sample for MALDI-TOF MS analysis. A Bruker Autoflex Speed MALDI-TOF/TOF MS (Bruker, Bremen, Germany) equipped with a Smartbeam laser (1000 Hz) was used for MALDI-TOF MS analysis. All data were collected in positive ion liner mode and analyzed by using Daltonics flexAnalysis 3.0 (Bruker).

Preparation of F8-Culture Pellet Suspension

F8-culture filtrate (100 ml) was centrifuged at 23000×g for 30 min. The supernatant was removed, and 100 ml of $H_2O$ was added to re-suspend the pellet. The re-suspended pellet was squeezed twice in a high-pressure homogenizer EF-C3 (Avestin EF-C3, Canada) at 20 kpsi. The final F8-culture pellet suspension was used for assay of induced plant resistance.

Determination of Molecular Weight of Polysaccharide

The molecular weight of polysaccharide was determined by using a Hitachi HPLC system equipped with an ELSD Detector (Alltech 3300, Grace) and two in-series TSK SuperAW2500 columns were used (6.0 mm×15 cm, Tosoh Bioscience LLC, Japan). The molecular weight standard kit (Polyethylene Glycol Standards Kit, PSS Polymer Standards GmbH, Germany) was used for calibration. In total, 10 μL of standard (1 mM) and purified polysaccharides were used for analysis (eluted with distilled $H_2O$; flow rate 0.1 mL/min). The standards with molecular weight 12600, 6550, 4270, and 1400 Da were eluted with the following tR: 36.5, 37.2, 38.4, and 43.2 min. The polysaccharide was eluted at 36.7 and 38.4 min. Example 1 Screening of culture filtrates derived from soil microorganisms for inducing plant resistance against Tobacco mosaic virus (TMV)

To identify PAMPs/DAMPs that can provide plant defense against viruses, we first collected soil samples at different locations and followed a previously reported method for microorganism isolation (Ko, W. H., Tsou, El, Lin, Mi, and Chern, L. L. 2010. *Activity and characterization of secondary metabolites produced by a new microorganism for control of plant diseases*. New biotechnology 27:397-402). We isolated 199 microorganisms including 77 actinomycetes, 68 bacteria and 54 fungi.

Figure 10:
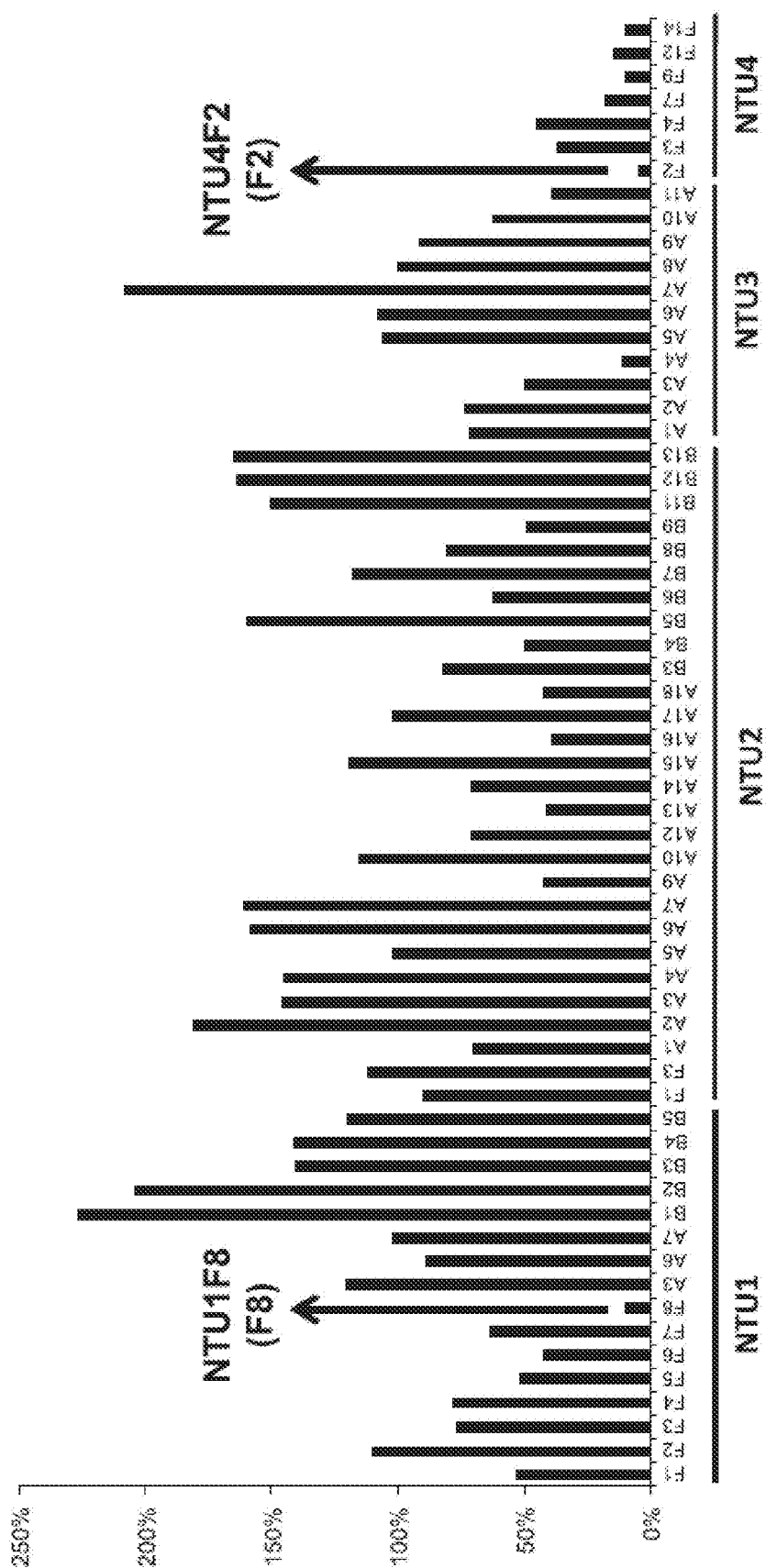
FIG. 10 shows screening of culture filtrates derived from soil microorganisms for inducing resistance to TMV in N. glutinosa. Soil microorganisms including actinomycetes, bacteria, and fungi were cultured with VB, and culture filtrates were collected. Each collected culture filtrate was sprayed on N. glutinosa three times at 24-h intervals. TMV was inoculated at 24 h post-treatment (hpt). Lesion numbers induced by TMV on leaves were counted at 5 days post-inoculation (dpi). Results are percentage of total lesion number induced by TMV in each culture filtrate to VB pretreatment. NTU1-4 indicates soil samples were collected at different locations. Isolated actinomycetes, bacteria, and fungi isolates are represented as A, B and C, respectively, followed by a number. Black arrow indicates fewer lesions induced by TMV with (F8)- and NTU4 F2 (F2)-culture filtrate pretreatment. A total of 199 microorganisms were isolated, including 77 actinomycetes, 68 bacteria and 54 fungi; only part of our analysis are presented here.

We selected TMV and its local lesion host *N. glutinosa* as a system for the initial screening. TMV can induce local lesions on *N. glutinosa*. The number and size of lesions reflects the degree of resistance to TMV (Loebenstein, 2009). The soil microorganisms were cultured in vegetable broth (VB) for 14 days, then culture filtrates were directly sprayed on *N. glutinosa* (0.4 ml per plant) for total of three times with a 24-h interval between each spray. Then, TMV inoculum was rubbed onto leaves of *N. glutinosa*. The lesion number was counted at 5 days post-inoculation (dpi). Because VB may contain DAMPs that trigger plant immunity, the results are represented as percentage lesion number induced by TMV on plants pretreated with culture filtrates from isolated microorganisms relative to VB-pretreated plants. Plants pretreated with culture filtrates from two fungi (F2 and F8) had fewer lesions than did VB-pretreated plants (FIG. 10).

To verify the ability of F2- and F8-culture filtrate to induce resistance in *N. glutinosa*, we treated plants with H$_2$O, SA, VB, F2- or F8-culture filtrate followed by TMV inoculation. All experiments were repeated at least 3 times, and the results were consistent, showing much reduced lesion numbers on *N. glutinosa* pretreated with F2- and F8-culture filtrate (FIGS. 1A and B).

Example 2 Demonstration of Exemplary F8-Culture Filtrate Induces Strong Resistance in *N. benthamiana*

Besides using *N. glutinosa* for our initial screening, we also used *N. benthamiana*, a host that is highly susceptible to TMV, for resistance assay. *N. benthamiana* was pretreated with H$_2$O, SA, VB, F2- or F8-culture filtrate as for pretreatment of *N. glutinosa*. All treated plants were inoculated with TMV inoculum made from lyophilized leaves of TMV infected *N. benthamiana*. Plants pretreated with H$_2$O, SA, VB and F2-culture filtrate showed severe symptoms; however, most plants with F8-culture filtrate pretreatment remained healthy looking (FIGS. 1C and D). With RT-PCR to detect TMV on all treated plants, the infection rate was much reduced with F8-culture filtrate than H$_2$O, SA, VB or F2-culture filtrate pretreatment (Table 1). In our repeat experiments, the infection rate of TMV-inoculated plants with F8-culture filtrate pretreatment even decreased to 0% (Table 1). In addition, plants with F8-culture filtrate pretreatment and TMV infection showed no obvious symptoms (FIG. 1D). We prepared at least 7 different batches of F8-culture filtrate, and the ability to induce resistance against TMV was consistent between different batches (Table 1). Of note, F2-culture filtrate did not induce resistance to TMV in *N. benthamiana* (Table 1, FIGS. 1C and D), so our later experiments focused on F8-culture filtrate.

TABLE 1

The infection rate of Tobacco mosaic virus (TMV) on
*Nicotiana benthamiana* with different pretreatments

| Pretreatment | Inoculum | Exp. 1 | Exp. 2 | Exp. 3 | Exp. 4 | Exp. 5 | Exp. 6 | Exp. 7 | Exp. 8 | Total |
|---|---|---|---|---|---|---|---|---|---|---|
| — | Buffer | 0/5[c] | 0/5 | 0/5 | 0/5 | 0/5 | 0/5 | 0/5 | 0/5 | 0/40 |
| H$_2$O[a] | TMV[b] | 5/5 | 5/5 | 5/5 | 5/5 | 5/5 | 5/5 | 5/5 | 5/5 | 40/40 |
| SA | TMV | 5/5 | 5/5 | 4/5 | 5/5 | 5/5 | 5/5 | 5/5 | 5/5 | 39/40 |
| VB | TMV | 5/5 | 5/5 | 5/5 | 4/5 | 5/5 | 5/5 | 5/5 | 5/5 | 39/40 |
| F2 | TMV | 5/5 | 5/5 | 5/5 | — | — | — | — | — | 15/15 |
| F8 | TMV | 1/5 | 0/5 | 0/5 | 1/5 | 0/5 | 1/5 | 0/5 | 0/5 | 3/40 |

[a]Plants pretreated with H$_2$O, 5 mM salicylic acid (SA), vegetable broth (VB) and culture filtrate derived from fungi F2 (F2) or fungi F8 (F8).
[b]Inoculum were made from lyophilized TMV-inoculated leaves.
[c]Number of plants detected with TMV to total TMV inoculated plants. All leaf samples were collected at 7 dpi, and TMV was detected by RT-PCR.

Experiments (Exp) were repeated at least 8 times. F8-culture filtrate used in Exp. 1-2 is from the same batch of preparation. F8-culture filtrate used in Exp. 3-8 was prepared individually.

In addition to using inoculum made from lyophilized leaves of TMV infected *N. benthamiana*, we also used different concentrations (1 μg/ml, 10 μg/ml and 50 μg/ml) of purified TMV particles as inoculum to inoculate *N. glutinosa* and *N. benthamiana* pretreated with H2O, SA, VB, or F8-culture filtrate (FIG. 2, FIG. 3). The results are consistent with previous results, which showed that TMV particle inoculated *N. glutinosa* and *N. benthamiana* showed less lesion and less disease severity in F8-culture filtrate treated *N. glutinosa* and *N. benthamiana*, respectively (FIGS. 2 and 3). The results also showed that increased TMV particle concentration positively correlated with increased lesion number and disease severity on leaves of F8-culture filtrate treated *N. glutinosa*, and *N. benthamiana*, respectively. The infection rate of TMV on *N. benthamiana* was also detected by use of qRT-PCR (Table 2). Reduced infection rate was only observed on F8-culture filtrate treated *N. benthamiana*, when TMV particle at the concentration of 1 μg/ml was used as inoculum (Table 2). Collectively, the data indicated that F8-culture filtrate can induce plant resistance to TMV infection, and increased concentration of TMV inoculum will increase the infectivity.

TABLE 2

The infection rate of Tobacco mosaic virus (TMV) particle
on *Nicotiana benthamiana* with different pretreatments

| | | Exp. 1 | | | Exp. 2 | Exp. 3 |
|---|---|---|---|---|---|---|
| Pretreatment | Inoculum | [a]1 μg/ml | [a]10 μg/ml | [a]50 μg/ml | [a]1 μg/ml | [a]1 μg/ml |
| — | Buffer | | 0/5[c] | | 0/3 | 0/3 |
| H$_2$O[b] | TMV particle | 6/6 | 6/6 | 6/6 | 6/6 | 9/9 |
| SA | TMV particle | 6/6 | 6/6 | 6/6 | 6/6 | 15/15 |
| VB | TMV particle | 6/6 | 6/6 | 6/6 | 6/6 | 15/15 |
| F8 | TMV particle | 4/6 | 6/6 | 6/6 | 3/6 | 6/15 |

[a]Plant were inoculated with difference concentration of TMV particle.
[b]Plants pretreated with H$_2$O, 5 mM salicylic acid (SA), vegetable broth (VB) and culture filtrate derived from fungi F8 (F8).
[c]Number of plants detected with TMV to total TMV inoculated plants. All leaf samples were collected at 7 dpi, and TMV was detected by RT-PCR.

Example 3 Demonstration of More Resistance with F8-Culture Filtrate than F8-Culture Pellets To investigate whether pellets of F8-culture also induce plant resistance against TMV, pellets of F8-culture were re-suspended with H$_2$O (same volume of original F8-culture). The re-suspended pellet was squeezed twice in a high-pressure homogenizer to break down the fungi cells. The final F8-culture pellet suspension, as well as H$_2$O, SA, VB or F8-culture filtrate, were used to pretreat *N. benthamiana* followed by inoculation with TMV as previously described. F8-pellet-treated plants showed mild symptoms, with no obvious symptoms seen with F8-culture filtrate pretreatment (FIGS. 11A and B). Even when the concentration of F8-pellets was doubled, the TMV-induced symptoms were still more severe than with F8-culture filtrate pretreatment (FIGS. 11A and B).

Example 4 Treating Local Leaves with F8-Culture Filtrate does not Protect Against Inoculation of the Upper Leaves To investigate whether F8-culture filtrate can protect plants systemically, we treated only the lower leaves (local) of N. benthamiana (method described above) with $H_2O$, SA, VB or F8-culture filtrate, and inoculated TMV in the upper untreated (systemic) leaves. As a control, we used F8-culture filtrate to treat whole plants followed by TMV inoculation. Whole plants pretreated with F8-culture filtrate showed much resistance to TMV (FIGS. 4A and B); however, all plants with pretreatment of only local leaves showed severe viral symptoms (FIGS. 4A and B). Therefore, F8-culture filtrate provides strong resistance in only treated leaves.

In another set of experiments, we pretreated local leaves of plants with $H_2O$, SA, VB or F8-culture filtrate, but did not inoculate them with TMV. We collected both the local and upper un-treated (systemic) leaves at 24 h post-treatment (hpt) to analyze the expression of the PR-1 gene (a SAR marker gene) (Zheng et al., 2015). PR-1 gene expression was detected in SA- and VB- but not F8-culture filtrate-treated local leaves (FIG. 4C). However, only SA-treated plants (positive control) showed increased PR-1 gene expression on systemic leaves (FIG. 4D). In addition, we collected leaves from plants with whole plants pretreated with $H_2O$, SA, VB or F8-culture filtrate. Consistently, PR-1 gene induction was detected in leaves of whole plants pretreated with SA and VB but not whole plants pretreated with F8-culture filtrate at 24 hpt (FIG. 4E). Thus, F8-culture filtrate does not induce canonical SAR.

To analyze whether F8-culture induces stronger resistance on TMV inoculated leaves infection, we inoculated TMV (1 µg/ml) on $H_2O$ or F8-culture filtrate pretreated leaves of N. benthamiana, and collected TMV-inoculated leaves at 24, 48, 72 and 96 h post-inoculation (hpi) to analyze the TMV accumulation and expression of the PR-1 gene by qRT-PCR. The data showed that in comparison to $H_2O$ treated plants, decreased TMV accumulation and increased PR1 expression were observed on F8-culture filtrate treated plants (FIG. 4F).

Example 5 Treatment with F8-Culture Filtrate Affects the Establishment of Initial TMV Infection To analyze which virus infection steps are affected in F8-culture filtrate-treated plants, we used TMV tagged with green fluorescence protein (GFP) to inoculate N. benthamiana and monitor the infection of TMV. Similar to our previous result, the infection rate of TMV-GFP was much reduced in N. benthamiana pretreated with F8-culture filtrate as compared with $H_2O$, SA or VB (Table S2). In addition, with TMV-GFP infection, the number of initial infection foci was reduced with both SA and F8-culture filtrate pretreatment (FIGS. 5A and B). To compare TMV-GFP accumulation in each foci, we used a puncher to collect GFP foci under UV light and used qRT-PCR to quantify the TMV-GFP expression. The mean TMV accumulation per foci was similar with $H_2O$, SA, VB and F8-culture filtrate pretreatment (FIG. 5C).

TABLE S2

The infection rate of TMV tagged with green fluorescence protein (TMV-GFP) on Nicotiana benthamiana with different pretreatments

| Inoculum | Exp. 1 | Exp. 2 |
|---|---|---|
| Buffer | 0/5[b] | 0/6 |
| TMV-GFP | 5/5 | 6/6 |
| TMV-GFP | 5/5 | 4/6 |
| TMV-GFP | 5/5 | 6/6 |
| TMV-GFP | 2/5 | 1/6 |

[a]Plants pretreated with $H_2O$, 5 mM salicylic acid (SA), vegetable broth (VB) and culture filtrate derived from fungi F8 (F8).
[b]Number of plants exhibiting green fluorescence under UV illumination to total TMV-GFP inoculated plants. Data were recorded at 7 dpi.
Two repeated experiments (Exp) were conducted.

To understand whether the cell-to-cell movement of TMV was affected with F8-culture filtrate pretreatment, we measured the average size of TMV-GFP infection foci at 5 and 7 dpi. In TMV-GFP-infected plants, the mean size of infection foci did not differ between plants with different pretreatment at 5 and 7 dpi ($P<0.05$) (FIGS. 5A and D).

To analyze whether long-distance movement is affected by F8-culture filtrate pretreatment, we measured the average time for TMV-GFP to move to apical leaves. The mean time (days) for TMV to move to apical leaves was similar with different pretreatments (FIGS. 5E and F).

Example 6 Demonstration of Exemplary F8-Culture Filtrate Induces Resistance to Turnip Mosaic Virus (TuMV) in Brassica juncea To analyze whether F8-culture filtrate induced resistance to different viruses in other plants, we treated plants from an economically important vegetable, Brassica juncea, with $H_2O$, VB and F8-culture filtrate by using the method mentioned above, and inoculated the plants with TuMV. TuMV induced severe mosaic and stunting symptoms in plants without any treatment or with VB pretreatment or induced severe mosaic symptoms in plants with $H_2O$ pretreatment (FIG. 6A); however, F8-culture filtrate pretreatment did not confer obvious symptoms (FIGS. 6A and B).

Example 7 F8-Culture Filtrate Pretreatment does not Cause Resistance-Associated Fitness Cost To analyze whether F8-culture filtrate pretreatment reduces resistance-associated fitness cost in plants, we analyzed the fresh weight and leaf area in untreated and F8-culture filtrate-treated N. benthamiana and Brassica juncea. Both F8-culture filtrate-treated and untreated N. benthamiana and Brassica juncea showed similar leaf area and fresh weight (FIGS. 6C and D).

Example 8 F8 Fungi is Most Related to Trichosporon scarabaeorum

Figures 7, 7A, 7B, 7C:
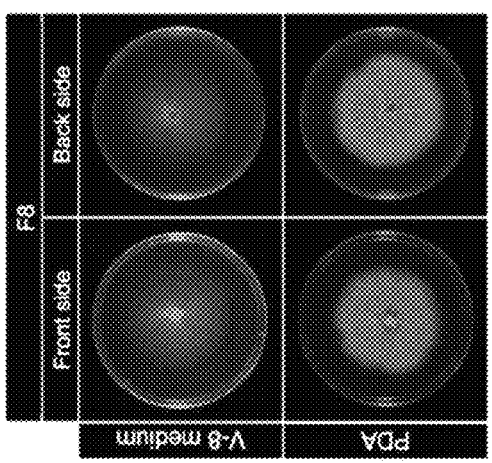
FIG. 7A to FIG. 7C show identification of F8 fungi. Phylogenetic tree of F8 fungi based on D1/D2 region (FIG. 7A) and ITS region (FIG. 7B) by neighbor-joining and maximum likelihood methods. The result using both analysis methods was similar, and only the neighbor-joining tree is shown here.

To identify the F8 fungi, we designed primers (Table S1) to amplify the D1/D2 domain and the ITS regions of the 26S rDNA (Scorzetti et al., 2002). Phylogenetic analysis was performed by neighbor-joining and maximum likelihood methods. The result using both methods was similar and indicated that F8 fungi is related to T. scarabaeorum (FIGS. 7A and B).

F8 is a yeast-like fungus. After culturing the fungi on PDA plate for 15 days, the diameter of colony grew to 54-57 mm. The colony of F8 is beige butter-like and wrinkled on PDA, but silk-like and flat on V-8 agar plate (FIG. 7C).

Under microscope observation, F8 generated arthroconidia. The arthroconidia were hyaline, short rod-shaped, and obovate (FIG. 7C). Together, molecular phylogenetic analysis of D1/D2 domain, ITS, and morphological features showed that our identified F8 fungus belongs to the basidiomycetous yeast, *T. scarabaeorum*.

TABLE S1

| | Primer sequence |
|---|---|
| TMV CP-F | CGTGTTCTTGTCATCAGCGT (SEQ ID NO: 1) |
| TMV CP-R | GCATCTAACGTTTCGGCAGT (SEQ ID NO: 2) |
| GFP-F | TACAAGACGCGTGCTGAAGT (SEQ ID NO: 3) |
| GFP-R | CAATGTTGTGGCGAATTTT (SEQ ID NO: 4) |
| CMV CA-F | ACGAACTGGTGATGCATTTACTTAT (SEQ ID NO: 5) |
| CMV CA-R | TTCCGAAGAAACCTAGGAGATGGTT (SEQ ID NO: 6) |
| ITS5e-F | TTAGAGGAAGTAAAAGTCGTAACAAGGTT (SEQ ID NO: 7) |
| ITS4e-R | TCCTCCGCTTATTGATATGCTTAAG (SEQ ID NO: 8) |
| LR1-F | GCATATCAATAAGCGGAGGAAAAG (SEQ ID NO: 9) |
| LR3-R | GGTCCGTGTTTCAAGACGG (SEQ ID NO: 10) |
| Nb PR-1-F | ATGCCCATAACAGCTCG (SEQ ID NO: 11) |
| Nb PR-1-R | GAGGATCATAGTTGCAAGAG (SEQ ID NO: 12) |
| Nb PR-2-F | GGTGTTTGCTATGGAATGC (SEQ ID NO: 13) |
| Nb PR-2-R | TCTGTACCCACCATCTTGC (SEQ ID NO: 14) |
| Nb PDF1.2-F | GGAAATGGCAAACTCCATGCG (SEQ ID NO: 15) |
| Nb PDF1.2-R | ATCCTTCGGTCAGACAAACG (SEQ ID NO: 16) |
| Nb PR-4-F | CAGAACATTAACTGGGATTTGAGAG (SEQ ID NO: 17) |
| Nb PR-4-R | CTCCATTTGCTGCATTGATCTACT (SEQ ID NO: 18) |
| Nb Osm-F | ACTTATGCTTCCGGCGTA (SEQ ID NO: 19) |
| Nb Osm-R | GCACCAGGGCATTCACCA (SEQ ID NO: 20) |
| Nb EREBP-F | GGGAAAACGGGTTTGGTTGGG (SEQ ID NO: 21) |
| Nb EREBP-R | CGTCAAAGTCAAACTCGCCGAATTC (SEQ ID NO: 22) |
| Nb β-actin-F | TGCCATTCTCCGTCTTGACT (SEQ ID NO: 23) |
| Nb β-actin-R | TGCAGTCTCGAGTTCCTGTT (SEQ ID NO: 24) |

Example 9 a Fraction of Polysaccharide Derived from F8-Culture Filtrate is the Major Active Component for Inducing Plant Virus Resistance To identify the active functional compound(s) in F8-culture filtrate that are responsible for inducing plant resistance, we separated the F8-culture filtrate by size-exclusion chromatography. Eight fractions (F8-fr1-8) were eluted by $H_2O$ with a Sephadex LH20 column. Each fraction was analyzed by MALDI-TOF MS, and the activity in inducing resistance against TMV was initially analyzed in *N. glutinosa*. Our repeat experiments indicated that the second fraction (F8-fr2) induced the strongest antiviral activity in *N. glutinosa* (FIG. 12A). To determine whether F8-fr2 also induced strong resistance in *N. benthamiana*, we treated *N. benthamiana* with F8-fr1-4, then inoculated plants with TMV (FIGS. 12B and C). Consistently, F8-fr2 induced the strongest antiviral activity in *N. benthamiana* (FIGS. 12B and 12C and Table S3), although the F8-culture filtrate still induced the best resistance (FIGS. 12B and 12C and Table S3).

TABLE S3

The infection rate of Tobacco mosaic virus (TMV) on *Nicotiana benthamiana* pretreated with different fractions derived from F8-culture filtrate

| Pre-treatment | Inoculum | Exp. 1 | Exp. 2 | Exp. 3 | Total |
|---|---|---|---|---|---|
| — | Buffer | 0/5[b] | 0/5 | 0/5 | 0/15 |
| $H_2O^a$ | TMV | 5/5 | 5/5 | 5/5 | 15/15 |
| SA | TMV | 5/5 | 5/5 | 5/5 | 15/15 |
| VB | TMV | 5/5 | 5/5 | 5/5 | 15/15 |
| F8 | TMV | 1/5 | 0/5 | 0/5 | 1/15 |
| F8-fr2 | TMV | 5/5 | 5/5 | 5/5 | 15/15 |
| F8-fr2-20% EtOH ppt | TMV | 5/5 | 5/5 | 5/5 | 15/15 |
| F8-fr2-50% EtOH ppt | TMV | 5/5 | 5/5 | 5/5 | 15/15 |
| F8-fr2-80% EtOH ppt | TMV | 5/5 | 5/5 | 5/5 | 15/15 |
| *1 | TMV | 5/5 | 5/5 | 5/5 | 15/15 |
| *2 (F8-polysaccharide) | TMV | 5/5 | 5/5 | 5/5 | 15/15 |
| *3 | TMV | 5/5 | 5/5 | 5/5 | 15/15 |

[a]Plants pretreated with $H_2O$, 5 mM salicylic acid (SA), vegetable broth (VB) and culture filtrate derived from fungi F8 (F8), F8-sephadex fraction 2 (F8-fr2), $H_2O$ re-suspended pellets derived from F8-fr2 precipitated with 20%, 50% and 80% ethanol (F8-fr2-20, 50 and 80% EtOH ppt) and HPLC purified peak 1 to 3 (*1 to 3*) from $H_2O$ re-suspended F8-fr2-80% EtOH ppt (Please see FIG. 10). We define peak *2 as F8-polysaccharide.
[b]The number of plants detected with TMV to the total TMV inoculated plants. All leaf samples were collected at 7 dpi, and TMV was detected by use of RT-PCR. Three repeated experiments were conducted.

Figure 13:
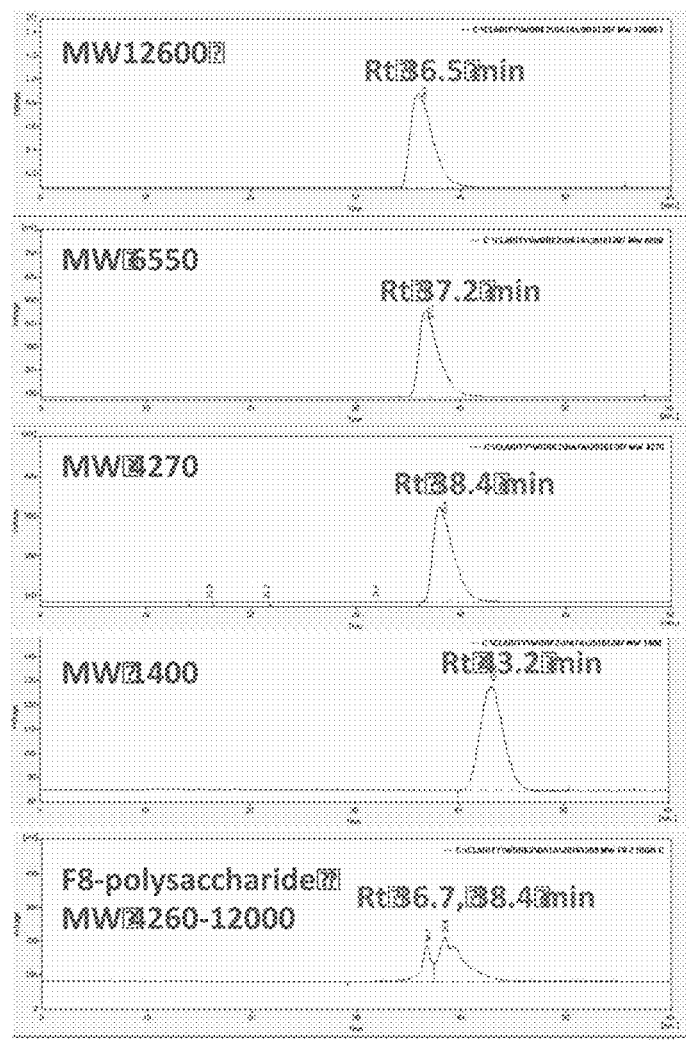
FIG. 13 shows molecular weight estimation of F8-polysaccharide using polyethylene glycol as standards by HPLC analysis. Column: Two TSK SuperAW2500 (each 15 cm×4.6 mm, 5 μm); Flow rate: 0.1 mL/min; Mobile phase: 100% dd$H_2O$; Detector: ELSD. MW 12600, Rt 36.5 min; MW6550, Rt 37.2 min; MW4270, Rt 38.4 min; MW1400, Rt 43.2 min; MW 4260-12000, Rt 36.7, 38.4 min).

On MALDI-TOF MS, F8-fr2 showed a polysaccharide signal, with no obvious signals observed after F8-fr4 (FIG. 12D). To purify F8-fr2 polysaccharides, we created three consecutive precipitations with increasing concentrations of ethanol (20%, 50% and 80%). The $H_2O$-re-suspended pellets derived from 80% ethanol precipitation (F8-fr2-80% EtOH ppt) exhibited the strongest antiviral activity (FIGS. 8A and B). Results of MALDI-TOF MS analysis suggested that F8-fr2-80% EtOH ppt mainly consists of polysaccharides (FIG. 8C). F8-fr2-80% EtOH ppt was further separated by high-performance liquid chromatography (HPLC) into 3 peaks (*1 to *3) (FIG. 8D). The *2 peak (designated F8-polysaccharide) showed the strongest antiviral activity (FIGS. 8A and B). The sugar composition of F8-polysaccharide was analyzed by gas chromatography mass spectrometry (GC-MS), which revealed D-mannose D-galactose and D-glucose in the ratio 1.0:1.2:10.0 (Table 3). Linkage analysis with GC-MS and NMR analysis suggested the F8-polysaccharide is mainly α-D-1,4-glucan (FIGS. 8E and F). The assignments of protons and carbons of the sample are in Table 3. HPLC analysis revealed the molecular weight of the F8-polysaccharide as 4.2 to 12.6 kD (FIG. 13).

TABLE 3

| Sugar composition (mol %) of F8-polysaccharide | | |
|---|---|---|
| D-Man | D-Gal | D-Glu |
| 1.0 | 1.2 | 10.0 |

Example 10 Demonstration of Exemplary F8-Polysaccharide Induces Priming of SA-Governed Immune Response Genes To analyze how F8-polysaccharide induces plant viral resistance, we measured the expression of SA-, JA- and ET-responsive immune marker genes in $H_2O$- and F8-polysaccharide-treated plants (Cortes-Barco et al., 2010; Milling et al., 2011; Zhu et al., 2014). We first confirmed the induction of marker genes induced by SA (PR-1 and PR-2), JA (PDF-1.2 and PR-4), and ET (Osm and EREBP) in *N. benthamiana* (FIG. 14A). Plants were pretreated with $H_2O$ and F8-polysacccharide for total of three times with a 24-h interval between each spray as described previously, then leaves were collected from one set of individual plants at 0, 12, 24, 36, 48, 72, and 96 hpt. In another set of plants with $H_2O$ and F8-polysacccharide pretreatment, TMV was inoculated at 24 hpt, and the inoculated leaves from individual plants were collected at 0, 12, 24, 48 and 72 hpi. We detected the accumulation of TMV and the expression of SA-, JA- and ET-responsive immune marker genes (FIG. 9A-D, FIGS. S5C and D). Consistently, TMV accumulation at 48 and 72 hpi was lower in F8-polysaccharide-than $H_2O$-pretreated plants in our three repeats (FIG. 14B). Inconsistent induction of PR-4 (JA marker gene) and Osmin (ET marker gene) was observed in the three repeats. Therefore, the expression of PR-4 and Osmin genes in *N. benthamiana* is not related to F8-polysaccharide treatment. The expression of PR-1, PR-2, PDF-1.2, and EREBP was consistent in our repeats (FIG. 9A-D, FIGS. 14C and D). A comparison of $H_2O$- and F8-polysaccharide-pretreated plants over different times showed that the expression of PR-1 was highly induced at 12 hpt and gradually reduced (FIG. 9A). However, after TMV inoculation, the expression of PR-1 was highly induced in plants treated with F8-polysaccharide at 48 and 72 hpi (FIG. 9B). The expression pattern of PR-2 was similar to that of PR-1 with or without TMV inoculation (FIGS. 9C and D). The expression of PR-1 and PR-2 show a typical priming expression pattern.

PDF-1.2 was induced at 12 hpt and 12 hpi but with no significant difference between $H_2O$- and F8-polysaccharide-pretreated plants in our repeated experiments (FIG. S5C). No significant induction of EREBP expression was observed in $H_2O$- and F8-polysaccharide-pretreated plants in our repeats (FIG. 14D).

We claim:

1. A method for inducing resistance to virus in a plant or priming a plant to resist viruses, or decreasing virus accumulation or increasing PR1 expression in a plant, comprising treating and/or contacting the plant with a biologically pure culture filtrate derived from fungi or a polysaccharide comprising D-mannose, D-galactose and D-glucose with a 1,4-glucan linkage, wherein the fungi is *Trichosporon* sp, and wherein the D-mannose, D-galactose and D-glucose are in the ratio about 0.5 to about 1.5:about 0.8 to about 2.0:about 8.0 to about 12.0.

2. The method of claim 1, wherein the *Trichosporon* sp. is *Trichosporon scarabaeorum*.

3. The method of claim 1, wherein the D-mannose, D-galactose and D-glucose has a α-1,4-glucan linkage.

4. The method of claim 1, wherein the ratio is about 1.0:about 1.2:about 10.0.

5. The method of claim 1, wherein the plant is *Nicotiana* or *Brassica*.

6. The method of claim 5, wherein the *Nicotiana* is *N. glutinosa* or *N. benthamiana*.

7. The method of claim 5, wherein the *Brassica* is *B. juncea*.

8. The method of claim 1, which does not induce canonical SAR.

9. The method of claim 1, wherein the virus is Tobacco mosaic virus, or Turnip mosaic virus.

* * * * *